(12) United States Patent
Winfield

(10) Patent No.: US 7,947,723 B2
(45) Date of Patent: May 24, 2011

(54) SYNTHESIS AND ANTI-PROLIFERATIVE EFFECT OF BENZIMIDAZOLE DERIVATIVES

(75) Inventor: Leyte L. Winfield, Austell, GA (US)

(73) Assignee: Spelman College, Atlanta, GA (US)

(*) Notice: Subject to any disclaimer, the term of this patent is extended or adjusted under 35 U.S.C. 154(b) by 0 days.

(21) Appl. No.: 12/363,168

(22) Filed: Jan. 30, 2009

(65) Prior Publication Data

US 2009/0197889 A1 Aug. 6, 2009

Related U.S. Application Data

(60) Provisional application No. 61/025,462, filed on Feb. 1, 2008.

(51) Int. Cl.
*A61K 31/415* (2006.01)
(52) U.S. Cl. .................................. 514/394; 548/310.7
(58) Field of Classification Search .................. 514/394; 548/310.7
See application file for complete search history.

(56) References Cited

U.S. PATENT DOCUMENTS

| | | | |
|---|---|---|---|
| 5,314,880 | A | 5/1994 | Whittaker et al. |
| 5,616,601 | A | 4/1997 | Khanna et al. |
| 5,723,485 | A | 3/1998 | Gungor et al. |
| 6,469,040 | B2 | 10/2002 | Seibert et al. |
| 6,613,789 | B2 | 9/2003 | Khanna et al. |
| 7,220,770 | B2 | 5/2007 | Khanna et al. |
| 2003/0036557 | A1 | 2/2003 | Khanna et al. |
| 2003/0134853 | A1 | 7/2003 | Priestley et al. |
| 2004/0067976 | A1 | 4/2004 | Priestley et al. |
| 2005/0096368 | A1 | 5/2005 | Khanna et al. |
| 2005/0256120 | A1 | 11/2005 | Khanna et al. |
| 2006/0135553 | A1 | 6/2006 | Campbell et al. |
| 2008/0249135 | A1 | 10/2008 | Slade et al. |
| 2009/0099179 | A1 | 4/2009 | Klein et al. |

FOREIGN PATENT DOCUMENTS

| | | |
|---|---|---|
| CN | 1506355 A | 6/2004 |
| IT | 663182 | 4/1964 |
| JP | 11060570 | 3/1999 |
| WO | WO 90/09997 | 9/1990 |
| WO | WO 9603388 A1 | 2/1996 |
| WO | WO 9805639 A1 | 2/1998 |
| WO | WO 03026587 A2 | 4/2003 |
| WO | WO 2006050162 A2 | 5/2006 |
| WO | WO 2006125539 A2 | 11/2006 |
| WO | WO 2006125540 A1 | 11/2006 |
| WO | WO 2007115306 A2 | 10/2007 |

OTHER PUBLICATIONS

Abdel-Monem, Wafaa R., "Synthesis and biological evaluations of sulfa derivatives bearing heterocyclic moieties," Department of Chemistry, Faculty of Education, Ain-Shams University, Cairo, Egypt. Bollettino Chimico Farmaceutico (2004), 143(6), 239-247. Publisher: Societa Editoriale Farmaceutica, CODEN: BCFAAI ISSN: 0006-6648. CAN 144:331292 AN 2005:534819 (Abstract).
Almansa, Carmen, et al., "Synthesis and SAR of a New Series of COX-2 Selective Inhibitors: Pyrazolo[1,5-a]pyrimidines," *Journal of Medicinal Chemistry*, 2001, vol. 44, No. 3, pp. 350-361.
Alvarez, F. J., et al., "3-phosphoinositide-dependent protein kinase-1/Akt signalling and inhibition in a canine prostate carcinoma cell line," Department of Veterinary Clinical Sciences, College of Veterinary Medicine, The Ohio State University, Columbus, OH, USA. Veterinary and Comparative Oncology (2007), 5(1), 47-58.
Alvarez, F. J., et al., "3-phosphoinositide-dependent protein kinase-1/Akt signalling and inhibition in a canine prostate carcinoma cell line," Department of Veterinary Clinical Sciences, College of Veterinary Medicine, The Ohio State University, Columbus, OH, USA. Veterinary and Comparative Oncology (2007), 5(2), 131 (Erratum).
*American Cancer Society.* "Cancer Facts & Figures 2009," Atlanta: American Cancer Society; 2009.
Bassignana, P., et al., "Infrared absorption spectra of certain imidazole and selenazole derivatives. Investigation of the C.dbd.N bonds," Spectrochimica Acta (1965), 21(3), 605-13. CODEN: SPACA5 ISSN: 0038-6987. CAN 62:48135 AN 1965:48135 (Abstract).
Bystrov, V.F., et al., "Reactivity constants of some 2-hetaryls," Inst. Org. Khim., Kiev, USSR. Zhurnal Obshchei Khimii (1968), 38(5), 1001-5. CODEN: ZOKHA4 ISSN: 0044-460X. Journal written in Russian. CAN 69:96568 AN 1968:496568 (Abtract).
Caron, Ruben W., et al., "Activated forms of H-RAS and K-RAS differentially regulate membrane association of PI3K, PDK-1, and AKT and the effect of therapeutic kinase inhibitors on cell survival," Departments of Radiation Oncology and Hematology/Oncology, Virginia Commonwealth University, Richmond, VA, USA. Molecular Cancer Therapeutics (2005), 4(2), 257-270.
Cen, L., et al., "PDK-1/AKT pathway as a novel therapeutic target in rhabdomyosarcoma cells using OSU-03012 compound," Center for Childhood Cancer, Columbus Children's Research Institute, Department of Pediatrics, Ohio State University, Columbus, OH, USA. British Journal of Cancer (2007), 97(6), 785-791.
Crowder, Robert J., et al., "Treating breast cancer through novel inhibitors of the phosphatidylinositol 3'-kinase pathway," Department of Medicine, Division of Oncology, Washington University School of Medicine and Siteman Cancer Center, St. Louis, MO, USA. Breast Cancer Research (2005), 7(5), 212-214.

(Continued)

*Primary Examiner* — James O Wilson
*Assistant Examiner* — Douglas M Willis
(74) *Attorney, Agent, or Firm* — Sutherland Asbill & Brennan LLP

(57) ABSTRACT

This invention provides for compounds, compositions, and methods that involve anti-proliferative and anti-neoplastic activity in cancer cells. In particular, a series of benzimidazole, purine, imidazopyridine, and imidazopyrizine compounds having selected substitution patterns are disclosed, and the activity of various subject compounds is demonstrated. For example, the invention provides compounds having the general formula:

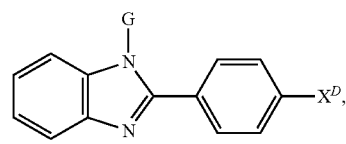

their pharmaceutical compositions, and methods of treatment using the subject compounds and compositions.

4 Claims, 1 Drawing Sheet

OTHER PUBLICATIONS

Cui, Wei, et al., "In-vivo effects and mechanisms of celecoxib-reduced growth of cyclooxygenase-2 (COX-2)-expressing versus COX-2-deleted human HCC xenografts in nude mice," *Anti-Cancer Drugs* 2008, vol. 19, No. 9, pp. 891-897.

Dent, Paul, et al., "DMC: novel celecoxib derivatives to rap cancer," Department of Biochemistry, Massey Cancer Center, Virginia Commonwealth University, Richmond, VA, USA. Cancer Biology & Therapy (2005), 4(5), 583-584.

Devarenne, Timothy P., et al., "Adi3 is a Pdk1-interacting AGC kinase that negatively regulates plant cell death," Boyce Thompson Institute for Plant Research, Ithaca, NY, USA. EMBO Journal (2006), 25(1), 255-265.

Evans, D., et al., "Synthesis of a group of 1H-benzimidazoles and their screening for antiinflammatory activity," *Eur J Med Chem* (1996) 31, 635-642.

Fichert, Thomas, "A Structure-Permeability Study of Small Druglike Molecules," *Bioorganic & Medicinal Chemistry letters* 13 (2003) 719-722.

Franke, Lutz, et al., "Extraction and Visualization of Potential Pharmacophore Points Using Support Vector Machines: Application to Ligand-Based Virtual Screening for COX-2 Inhibitors," *Journal of Medicinal Chemistry*, 2005, vol. 48, No. 22, pp. 6997-7004.

Gao, Ming, et al., "OSU-03012, a Novel Celecoxib Derivative, Induces Reactive Oxygen Species-Related Autophagy in Hepatocellular Carcinoma," *Cancer Res* 2008; 68:(22), Nov. 15, 2008, pp. 9348-9357.

Gieselman, Melinda B., et al., "Water-soluble polybenzimidazole-based polyelectrolytes," *Macromolecules*, 1992, 25 (18), 4832-4834.

Haiming, Ding, et al., "OSU03012 activates Erk1/2 and Cdks leading to the accumulation of cells in the S-phase and apoptosis," Department of Radiology, College of Medicine, The Ohio State University, Columbus, OH 43210, USA. International journal of cancer. Journal international du cancer (2008), 123(12), 2923-30.

Haiming, Ding, et al., "Sensitivity to the non-COX inhibiting celecoxib derivative, OSU03012, is p21(WAF1/CIP1) dependent," Department of Radiology, College of Medicine, The Ohio State University, Columbus, OH 43210, USA. International journal of cancer. Journal international du cancer (2008), 123(12), 2931-8.

Jerchel, Dietrich, et al., "Preparation of benzimidazoles," Johannes Gutenberg Univ., Mainz, Germany. Annalen der Chemie, Justus Liebigs (1952), 575 162-73. CODEN: 9X224Y CAN 47:15855 AN 1953:15855 (Abstract).

Johnson, Amy J., et al., "A novel celecoxib derivative, OSU03012, induces cytotoxicity in primary CLL cells and transformed B-cell lymphoma cell line via a caspase- and Bcl-2-independent mechanism," Division of Hematology and Oncology, Department of Internal Medicine, The Ohio State University, Columbus, OH, USA. Blood (2005), 105(6), 2504-2509.

Junan, Li, et al., "A structurally optimized celecoxib derivative inhibits human pancreatic cancer cell growth," Departments of Surgery and Internal Medicine, College of Medicine, The Ohio State University, 410 West 10th Avenue, Columbus, OH 43210, USA Journal of gastrointestinal surgery : official journal of the Society for Surgery of the Alimentary Tract (2006), 10(2), 207-14.

Kardosh, Adel, et al., "Dimethyl-Celecoxib (DMC), a Derivative of Celecoxib that Lacks Cyclooxygenase-2-Inhibitory Function, Potently Mimics the Anti-Tumor Effects of Celecoxib on Burkitt's Lymphoma In Vitro and In Vivo," Cancer Biology & Therapy (2005), 4(5), 571-582.

Kazanov, Diana, et al., "Celecoxib But Not Rofecoxib Inhibits the Growth of Transformed Cells in Vitro, " *Clinical Cancer Research*, vol. 10, 267-271, Jan. 1, 2004.

Koshienko, Yu. V., et al., "Benzo[1,2-d:3,4-d']diimidazole derivatives. II. Behavior of 3,6-dimethyl- and 3,6,7-trimethylbenzo[1,2-d:3,4-d']diimidazole toward nucleophilic agents," Rostov-on-Don, USSR. Khimiya Geterotsiklicheskikh Soedinenii (1971), 7(8), 1123-5. CODEN: KGSSAQ ISSN: 0132-6244. CAN 77:19030 AN 1972:419030 (Abstract).

Kucab, Jill E., et al., "Celecoxib analogues disrupt Akt signaling, which is commonly activated in primary breast tumours," British Columbia Research Institute for Children's and Women's Health, Department of Pediatrics, University of British Columbia, Vancouver, BC, Can. Breast Cancer Research (2005), 7(5), R796-R807.

Lei, Xin Sheng, et al., "Selective Cyclooxygenase-2 Inhibitors: Design and Synthesis," *Chinese Chemical Letters*, vol. 10, No. 6, pp. 469-472, 1999.

Li, Meiying, et al., "Synthesis of 2-cyclohexyl-1-[4-(methylsulfonyl)phenyl]-1H-benzimidazole derivatives and 4,5,6,7-tetrahydro-1-[4-(methylsulfonyl)phenyl]-2-phenyl-1H-benzimidazole derivatives and determination of their activity as COX-2 inhibitors." Institute of Pharmacology and Toxicology, Academy of Military Medical Science, Beijing, Peop. Rep. China. Zhongguo Yaowu Huaxue Zazhi (2006), 16(5), 284-288. Publisher: Zhongguo Yaowu Huaxue Zazhi Bianjibu, CODEN: ZYHZEF ISSN: 1005-0108. CAN 149:513735 AN 2007:1461095 (Abstract).

Li, Mei-Ying, et al., "Synthesis of N-Aryl-2-substituted Tetrahydrobenzimidazoles via Direct N-Arylation," *Synthetic Communications*, 37: 1001-1009, 2007.

McCubrey, James A., et al., "OSU-03012 in the treatment of glioblastoma," Department of Microbiology and Immunology, Brody School of Medicine at East Carolina University, Greenville, NC, USA. Molecular Pharmacology (2006), 70(2), 437-439.

Mukherjee, Pinku, et al., "Progression of Pancreatic Adenocarcinoma Is Significantly Impeded with a Combination of Vaccine and COX-2 Inhibition," *The Journal of Immunology*, 2009, pp. 216-224.

Park, Margaret A., et al., "OSU-03012 stimulates PKR-like endoplasmic reticulum-dependent increases in 70-kDa heat shock protein expression, attenuating its lethal actions in transformed cells," Department of Biochemistry, Virginia Commonwealth University, Richmond, VA, USA. Molecular Pharmacology (2008), 73(4), 1168-1184.

Park, Margaret A., et al., "PERK-dependent regulation of HSP70 expression and the regulation of autophagy," Department of Biochemistry and Molecular Biology, Virginia Commonwealth University, Richmond, VA, USA. Autophagy (2008), 4(3), 364-367.

Porchia, Leonardo M., et al., 2-Amino-N-{4-[5-(2-phenanthrenyl)-3-(trifluoromethyl)-1H-pyrazol-1-yl]-phenyl} acetamide (OSU-03012), a celecoxib derivative, directly targets p21-activated kinase, Division of Medicinal Chemistry and Pharmacognosy, The Ohio State University Colleges of Medicine and Pharmacy and the Arthur G. James Comprehensive Cancer Center, Columbus, OH, USA. Molecular Pharmacology (2007), 72(5), 1124-1131.

*Rapid Commun. Mass Spectrom.*, Letter to the Editor, 2004; 18: 584-587.

Ryan, Elizabeth P., et al., "Cyclooxygenase-2 independent effects of cyclooxygenase-2 inhibitors on oxidative stress and intracellular glutathione content in normal and malignant human B-cells," Department of Environmental Medicine, Lung Biology and Disease Program, University of Rochester School of Medicine and Dentistry, 601 Elmwood Avenue, Box 850, Rochester, NY 14642, USA, Cancer immunology, immunotherapy : CII (2008), 57(3), 347-58.

Schönthal, Axel H., et al., "Celecoxib analogs that lack COX-2 inhibitory function: preclinical development of novel anticancer drugs," Department of Molecular Microbiology and Immunology, University of Southern California, Los Angeles, CA, USA. Expert Opinion on Investigational Drugs (2008), 17(2), 197-208.

Seto, Shuichi, et al., "Reactions of tropoids and quinone derivatives. III. Reaction of several tropolones with o-benzoquinone di-benzimide," Tohoku Univ., Sendai, Bulletin of the Chemical Society of Japan (1962), 35 1010-14. CODEN: BCSJA8 ISSN: 0009-2673. CAN 57:75937 AN 1962:475937 (Abstract).

Szabo, Imre L., et al., "NSAIDs inhibit the activation of egr-1 gene in microvascular endothelial cells. A key to inhibition of angiogenesis?," *Journal of Physiology*—Paris 95 (2001) 379-383.

Tetko, Igor V., et al., "Application of ALOGPS to Predict 1-Octanol/Water Distribution Coefficients, logP, and logD, of AstraZeneca In-House Database," *Journal of Pharmaceutical Sciences*, vol. 93, No. 12, Dec. 2004, pp. 3103-3109.

To, K., et al, "The phosphoinositide-dependent kinase-1 inhibitor 2-amino-N-[4-[5-(2-phenanthrenyl)-3-(trifluoromethyl)-1H-pyrazol-1-yl]phenyl]-acetamide (OSU-03012) prevents Y-box binding protein-1 from inducing epidermal growth factor receptor," Laboratory for Oncogenomic Research, Department of Pediatrics, Child and Family Research Institute, University of British Columbia, Vancouver, BC, Can. Molecular Pharmacology (2007), 72(3), 641-652.

Tseng, Ping-Hui, et al., Overcoming trastuzumab resistance in HER2-overexpressing breast cancer cells by using a novel celecoxib-derived phosphoinositide-dependent kinase-1 inhibitor,Division of Medicinal Chemistry and Pharmacognosy, College of Pharmacy, The Ohio State University, Columbus, OH, USA. Molecular Pharmacology (2006), 70(5), 1534-1541.

Tseng, Ping-Hui, et al., "Synergistic interactions between imatinib mesylate and the novel phosphoinositide-dependent kinase-1 inhibitor OSU-03012 in overcoming imatinib mesylate resistance," Division of Medicinal Chemistry, College of Pharmacy, The Ohio State University, Columbus, OH, USA. Blood (2005), 105(10), 4021-4027.

Wang, Yu-Chieh, et al., "Targeting Endoplasmic Reticulum Stress and Akt with OSU-03012 and Gefitinib or Erlotinib to Overcome Resistance to Epidermal Growth Factor Receptor Inhibitors," *Cancer Res* 2008; 68: (8). Apr. 15, 2008, pp. 2820-2830.

Weng, Shu-Chuan, et al., "Sensitizing estrogen receptor-negative breast cancer cells to tamoxifen with OSU-03012, a novel celecoxib-derived phosphoinositide-dependent protein kinase-1/Akt signaling inhibitor," Division of Medicinal Chemistry and Pharmacognosy, College of Pharmacy, and Division of Hematology and Oncology, Department of Internal Medicine, College of Medicine, The Ohio State University, Columbus, OH, USA. Molecular Cancer Therapeutics (2008), 7(4), 800-808.

Wilford, J. B., et al., "The Infrared Spectra of Pentacarbonyl Fluoroalkylmanganese and-rhenium Complexes in the Carbonyl Stretching Region," *Inorganic Chemistry*, vol. 4, No. 3, Mar. 1965, pp. 389-393.

Winfield, Leyte L., et al., "A Preliminary Assessment of the Structure-Activity Relationship of Benzi-midazole-Based Anti-Proliferative Agents," *Letters in Drug Design & Discovery*, 2008, 5, 369-376.

Yacoub, Adly, et al., "OSU-03012 promotes caspase-independent but PERK-, cathepsin B-, BID-, and AIF-dependent killing of transformed cells," Department of Biochemistry, Virginia Commonwealth University, Richmond, VA, USA. Molecular Pharmacology (2006), 70(2), 589-603.

Zhang, Rui-ping, et al., "Characteristic elimination reactions of 1,2-disubstituted phenylbenzimidazoles and their isosteres 2,3-disubstituted phenylindoles in electron ionization mass spectrometry," Inst. of Materia Medica, Chinese Acad. of med. Sci. and Peking Union Med. Coll., Beijing, Peop. Rep. China. Rapid Communications in Mass Spectrometry (2004), 18(5), 584-587. Publisher: John Wiley & Sons Ltd., CODEN: RCMSEF ISSN: 0951-4198. CAN 140:374830 AN 2004:184538 (Abstract).

Zhang, Shuhong, et al., "OSU-03012, a Novel Celecoxib Derivative, Is Cytotoxic to Myeloma Cells and Acts through Multiple Mechanisms," Division of Hematology and Oncology, Department of Internal Medicine, Indiana University School of Medicine, Indianapolis, IN, USA. Clinical Cancer Research (2007), 13(16), 4750-4758.

Zhimin, Tong, et al., "Neutrophil gelatinase-associated lipocalin as a survival factor," Division of Pharmacology and Toxicology, College of Pharmacy, The University of Texas at Austin, Austin, TX, USA. The Biochemical journal (2005), 391(Pt 2), 441-8.

Zhu, Jiuxiang, et al., "From the Cyclooxygenase-2 Inhibitor Celecoxib to a Novel Class of 3-Phosphoinositide-Dependent Protein Kinase-1 Inhibitors," Cancer Research 64, 4309-4318, Jun. 15, 2004.

SYNTHESIS AND ANTI-PROLIFERATIVE EFFECT OF BENZIMIDAZOLE DERIVATIVES

This application claims the benefit of U.S. Provisional Application No. 61/025,462, filed Feb. 1, 2008, the disclosure of which is incorporated herein by reference in its entirety.

GOVERNMENT LICENSE RIGHTS

The U.S. Government has a paid-up license in this invention and the right in limited circumstances to require the patent owner to license others on reasonable terms as provided for by the terms of Grant No. 5P20MD000215-070002 awarded by the National Institutes of Health, National Center on Minority Health and Health Disparities, to Spelman College.

FIELD OF THE INVENTION

The invention is related to compounds, compositions, and methods that involve anti-proliferative and anti-neoplastic activity in cancer cells.

BACKGROUND OF THE INVENTION

It is estimated that 10.1 million Americans have a medical history that involves cancer, and it is expected that another 1.4 million new cases will develop in the next year. Cancer is the second leading cause of death among Americans, with prostate cancer being the leading form found in men. Unfortunately, the statistics surrounding the disease are complicated by disparities relating to race and sex and by declining relative survival rates. For general information, see: American Cancer Society, *Cancer Facts and Figures* 2008, Atlanta: American Cancer Society, 2008.

Prostate cancer, which is being increasingly diagnosed in younger-aged men, often metastasizes to other places in the body and therefore is difficult to regulate. Studies have shown that the cellular survival pathways present in the cancerous tissues of the prostate, and where it spreads in the body, are resistant to the normal apoptosis processes that constitute a principal type of programmed cell death (PCD) in a complex organism. Thus, cancerous cells are able to avoid apoptosis and replicate in an unregulated manner, causing malignant tumors to form. Some causes for the rapid cell growth in the prostates of men are due to age and the presence of mutated genes that encode proteins for cell division. See: Kleinsmith, L. J., *Principles of Cancer Biology*, Pearson Benjamin Cummings (2006). Further, studies of the genetic make up of African American males diagnosed with prostate cancer have associated an over-expression of the gene Bcl-2 that prevents apoptosis with the cancer. Moreover, Bcl-2 has also been linked to other fatal cancers like breast cancer and leukemia in children.

Celecoxib, an FDA-approved drug, is known to induce apoptosis by inhibiting the PDK1/Akt interaction in a process independent of its cyclooxygenase-2 (COX-2) activity. Its PDK1 activity has been directly linked to its ability to inhibit cell growth in prostate cancer cells. Exploiting the activity of celecoxib, Zhu et al. developed a library of molecules which included the efficacious compound known as OSU-03013. This celecoxib derivative diminished cell proliferation by inhibiting PDK1 in PC-3 cells in micromolar concentrations thirty-fold lower than that of celecoxib. The versatility of OSU-03013 in treating a number of tumors, and its ability in overcoming the chemotherapeutic resistance of some drugs have been noted.

While the activity of these compounds has been attributed to their binding to the catalytic domain of PDK1 and the subsequent inhibition of Akt activation, the mechanism of action has not been fully identified. Further, the ability of celecoxib to inhibit cell proliferation has been attributed to mechanisms associated with the reduction of inflammations and the inhibition of the COX-2 enzyme. See: Cui, W. et al., *Anti-Cancer Drugs* (2008), 19(9), 891-897; Szabo, I. et al., *J. Phys. (Paris)*, 2001, 95, 379-383; Yoshinaka, R. et al., *Anticancer Research* (2006), 26(6B), 4245-4254; and Mukherjee, P. et al., *J. of Immunology* (2008), Volume Date 2009, 182(1), 216-224. In comparison to other, more potent COX-2 inhibitors, celecoxib displayed a superior potency in inducing apoptosis in comparison to other COX-2 inhibitors. See: Kazanov, D. et al., *Clin. Cancer Res.,* 2004, 10, 267-271; and Srinath, P. et al., *Anticancer Res.,* 2003, 23, 3923-3928. The compound's ability to induce apoptosis by various routes adds to its appeal as a chemotherapeutic agent and a lead molecule. Analogs of celecoxib could potentially be active against malignant growth and be useful as a Non-steroidal Anti-inflammatory Drug (NSAID) with enhanced oral activity and superior safety to that of celecoxib. Such a molecule would vastly improve the treatments for cancer and inflammation based diseases.

Thus, new compounds are needed that might function in a fashion similar to celecoxib and possibly help identify the structural and electronic features of a molecule that give rise to such activity. In addition, new compounds are needed that might exhibit anti-proliferative or anti-neoplastic activity, regardless of the specific mechanism by which such activity might arise. Therapeutically effective agents, particularly those that are effective in humans and other mammals, are needed to treat such diseases, to increase the survivability of the patient, inhibit the rapidly-proliferating cell growth associated with the neoplasm, and/or effect a regression of the neoplasm.

BRIEF SUMMARY OF THE INVENTION

In one aspect, the present invention provides a series of compounds that exhibit anti-proliferative activity, including activity against human prostate cancer cells. Therefore, methods for treating and/or preventing a neoplasia are provided herein. The compounds disclosed herein include substituted benzimidazole, purines, imidazopyridine, and imidazopyridine species, which are shown to inhibit cell proliferation in PC-3 cells. This invention also provides methods of making the inventive compounds, and methods of treating and/or preventing cancer using the inventive compounds.

As used herein, the term "treatment" is non-limiting and includes the partial or total inhibition of the neoplasia growth, spreading, or metastasis, or partial or total destruction of the neoplasia cells. The term "prevention," as used herein, is also non-limiting, and includes either preventing the onset of clinically evident neoplasia altogether, or preventing the onset of a preclinically evident stage of neoplasia in individuals at risk. The prevention of initiation for malignant cells or arresting or reversing the progression of premalignant cells to malignant cells are also intended to be encompassed by this definition. Therefore, prevention includes the prophylactic treatment of those at risk of developing the neoplasia. Also as used herein, the phrase "therapeutically-effective," as in describing a therapeutically-effective amount of a drug or dosage form, is intended to qualify an amount of an agent that will achieve the goal of improvement in disease severity or the frequency of incidence. Typically, the phrase therapeutically-effective involves the minimization or, if possible, the avoidance of adverse side effects associated with many therapies. The term "neoplasia" is intended to be non-limiting, and includes any abnormal new growth, or tumor, which may be benign or malignant. Thus, neoplasia includes, but is not limited to, neoplasia that produce prostaglandins or express a cyclooxygenase, including benign and cancerous tumors, growths, and polyps.

In one aspect, this invention provides a compound having the formula:

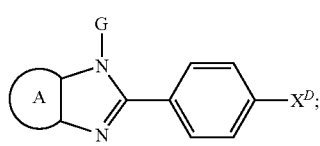

(I)

wherein

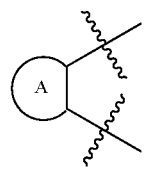

is selected from:

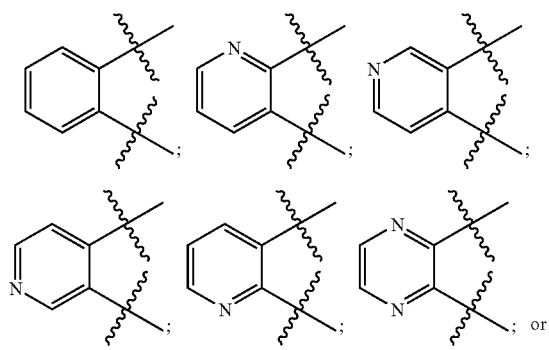

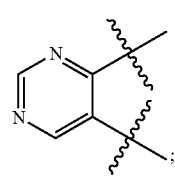

wherein G is selected from

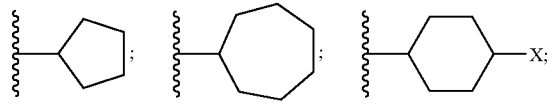

-continued

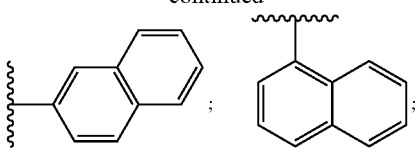

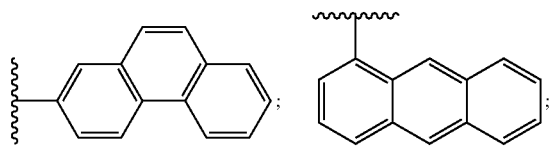

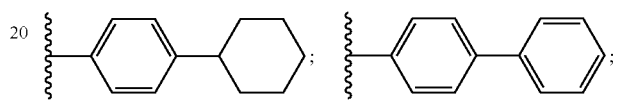

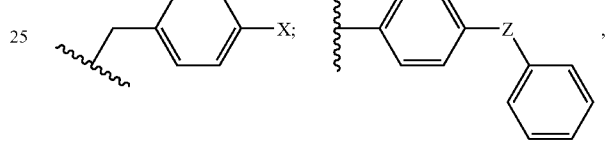

wherein Z is selected from $CH_2$, NH, O, or S;

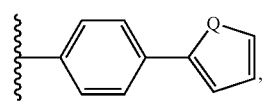

wherein Q is selected from $CH_2$, NH, O, or S;

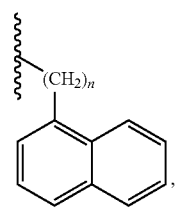

wherein n is 0, 1, 2, or 3; or

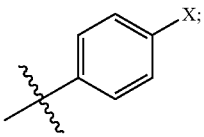

wherein X in each occurrence is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide;

wherein $X^D$ is selected from

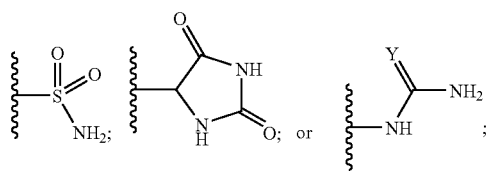

and Y is selected from O, or NH.

In one aspect, this invention provides a compound based on (I) having the formula:

(1)

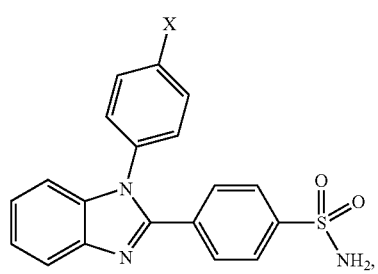

(2)

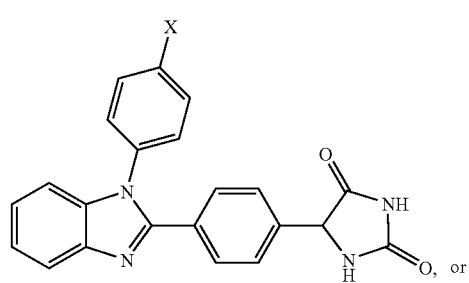

(3)

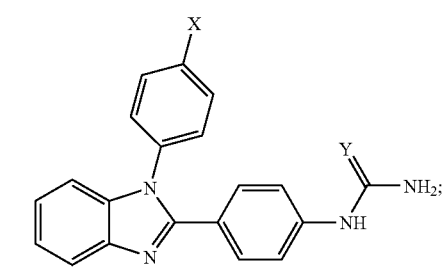

wherein Y is selected from O or NH; and X is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide. For instance, X can be $X^A$, wherein $X^A$ is selected from H, $CH_3$, $C(CH_3)_3$, $CF_3$, $OCF_3$, $C_6H_5$, $OCH_3$, $OC(CH_3)_3$, or Cl.

An additional aspect of the invention provides a compound based on (I) having the formula:

(4)

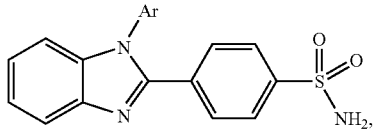

(5)

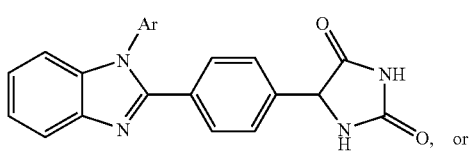

(6)

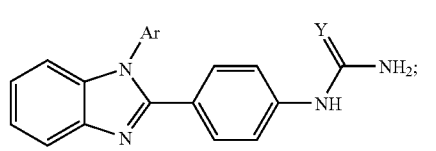

wherein Ar can be selected from:

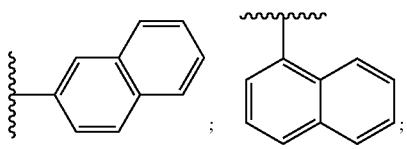

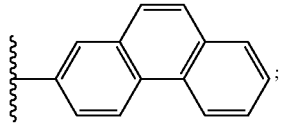

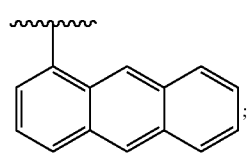

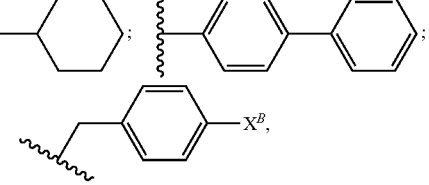

wherein $X^B$ can be $CH_3$, $C(CH_3)_3$, or $OCH_3$;

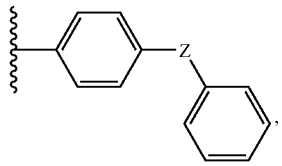

wherein Z can be CH$_2$, NH, O, or S;

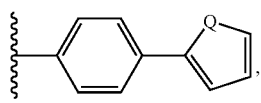

wherein Q can be CH$_2$, NH, O, or S; or

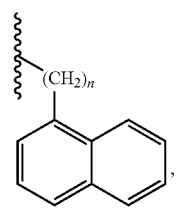

wherein n can be 0, 1, 2, or 3; and Y can be selected from O or NH.

Additionally, the invention provides a compound based on (I) having the formula:

(7)
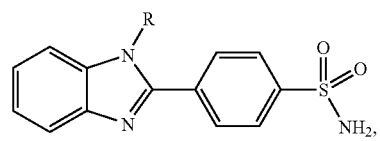

(8)
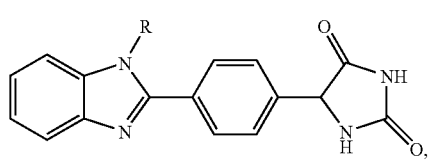

or (9)
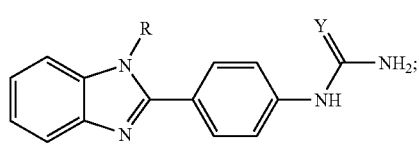

wherein R can be

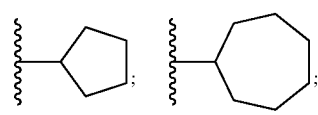

or

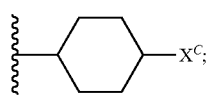

wherein X$^C$ can be H, CH$_3$, or C(CH$_3$)$_3$; and Y can be selected from O or NH.

In yet another aspect, this invention also provides a compound based on (I) having the formula:

(10)
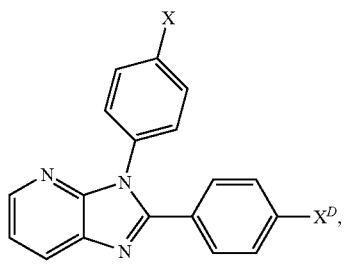

(11)
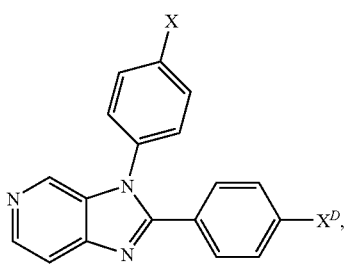

(12)
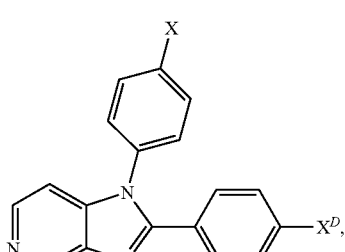

(13)
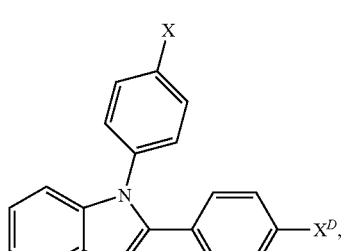

(14)
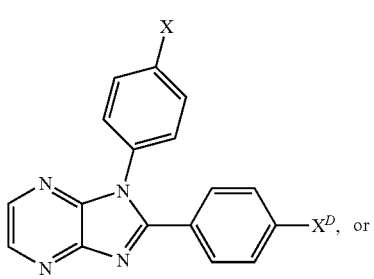

or (15)

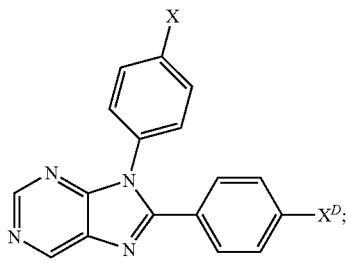

wherein X is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide; $X^D$ can be

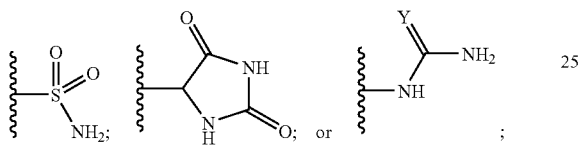

and wherein Y can be selected from O or NH. For instance, X can be $X^A$, wherein $X^A$ is selected from H, $CH_3$, $C(CH_3)_3$, $CF_3$, $OCF_3$, $C_6H_5$, $OCH_3$, $OC(CH_3)_3$, or Cl.

In yet another aspect, this invention also provides a compound based on (I) having the formula:

(16)
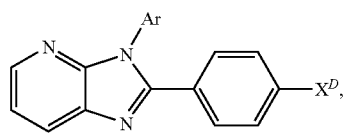

(17)
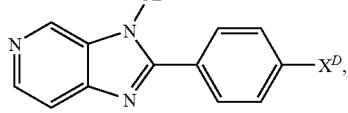

(18)
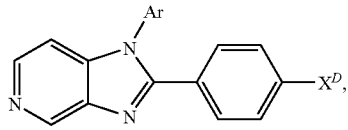

(19)
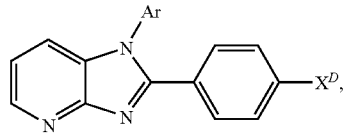

(20)
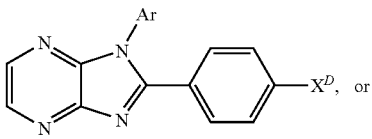 or

(21)
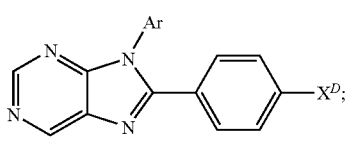

wherein Ar can be selected from

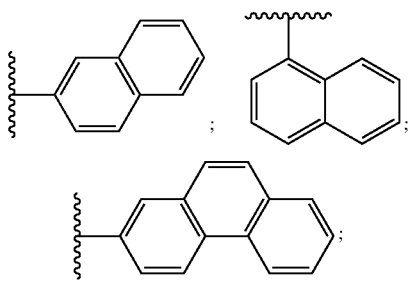

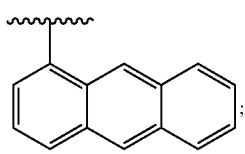

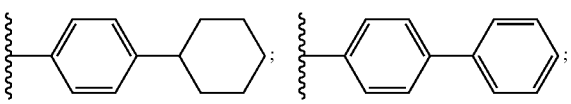

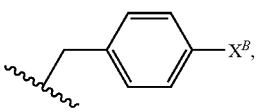

wherein $X^B$ can be $CH_3$, $C(CH_3)_3$, or $OCH_3$;

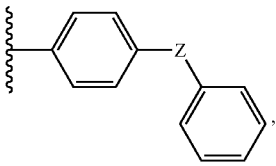

wherein Z can be $CH_2$, NH, O, or S;

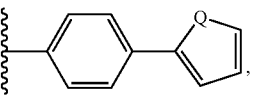

wherein Q can be CH$_2$, NH, O, or S;
or

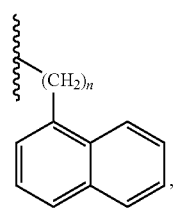

wherein n can be 0, 1, 2, or 3;
X$^D$ can be

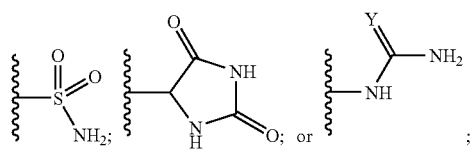

and wherein Y can be selected from O or NH.

In another aspect, this invention provides a compound of the formula:

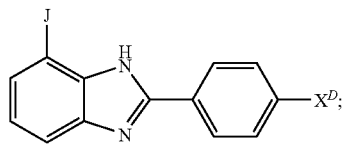 (II)

wherein J is selected from

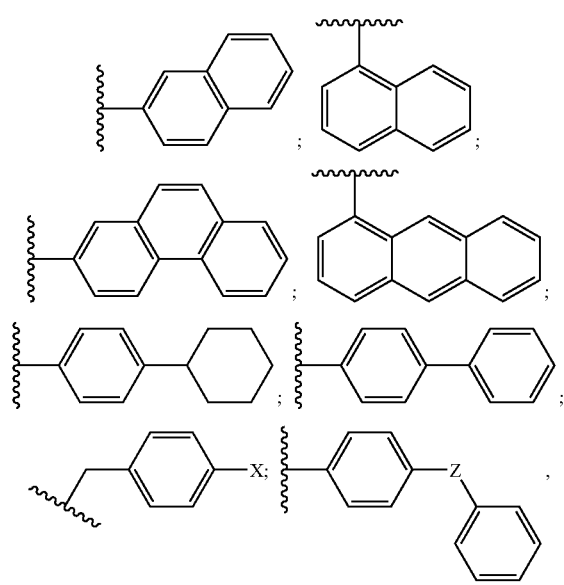

wherein Z is selected from CH$_2$, NH, O, or S;

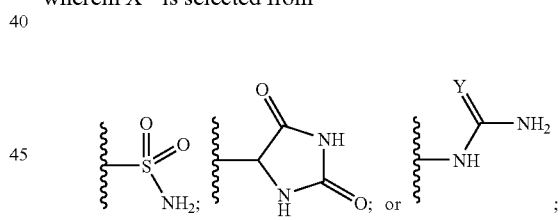

wherein Q is selected from CH$_2$, NH, O, or S;

wherein n is 0, 1, 2, or 3; or wherein X in each occurrence is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide;

wherein X$^D$ is selected from and Y is selected from O or NH.

Further, this invention also provides a compound based on (II) having the formula:

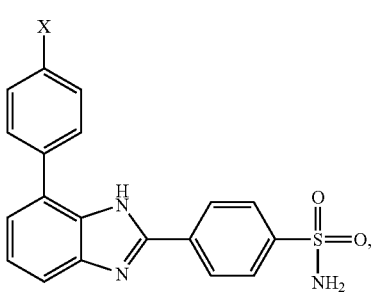 (22)

-continued

(23)
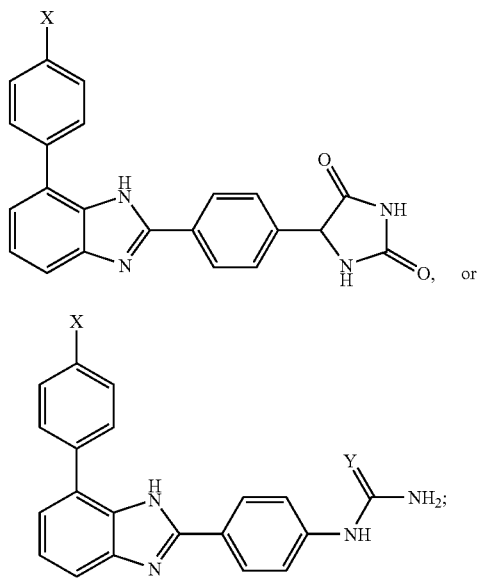

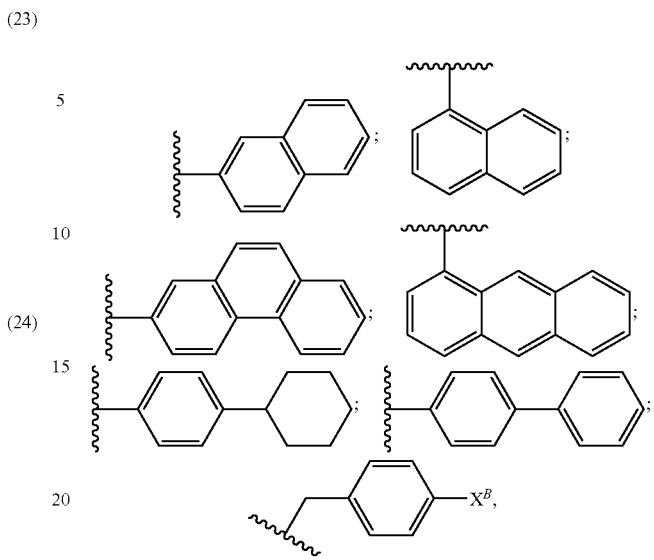

wherein Ar can be selected from wherein $X^B$ can be $CH_3$, $C(CH_3)_3$, or $OCH_3$;

wherein X is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide; and wherein Y can be selected from O or NH. For instance, X can be $X^A$, wherein $X^A$ is selected from H, $CH_3$, $C(CH_3)_3$, $CF_3$, $OCF_3$, $C_6H_5$, $OCH_3$, $OC(CH_3)_3$, or Cl.

A further aspect of this invention provides for a compound based on (II) having the formula:

(25)
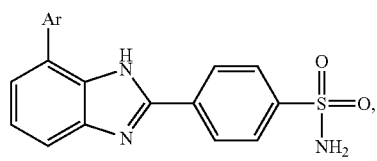

wherein Z can be $CH_2$, NH, O, or S;

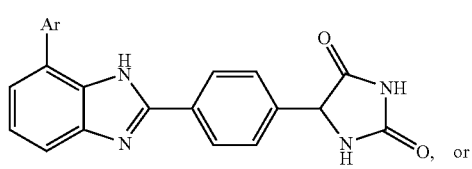

wherein Q can be $CH_2$, NH, O, or S; or

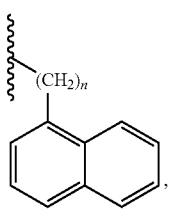

(26)

(27)
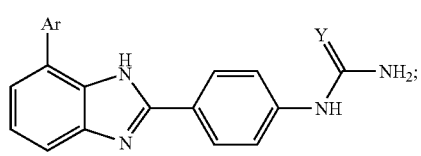

wherein n can be 0, 1, 2, or 3; and Y can be selected from O or NH.

Yet another aspect of this invention provides for a pharmaceutical composition comprising a therapeutically-effective amount of at least one compound according to the present disclosure, or a pharmaceutically-acceptable salt thereof, and a pharmaceutically-acceptable carrier. This composition may also comprise other pharmaceutically-acceptable excipients, stabilizers, diluents, adjuvants, preservatives, binders, coatings, disintegrants, sorbants, or other suitable additives or components as understood by one of ordinary skill in the art.

Still another aspect of this invention provides for a method of treating a neoplasia of any type in a mammalian subject, the method comprising treating the subject with a therapeutically-effective amount of at least one compound according to the present disclosure, or a pharmaceutically-acceptable salt thereof. This method includes treating the subject with a therapeutically-effective amount of a composition comprising the compound, as disclosed herein.

In another aspect, the present invention provides a method of making a compound according to any of formulas 1 through 27, as illustrated herein. The method of this disclosure can include the synthesis, purification, and/or isolation of the desirable compound.

These and other aspects of the present invention are provided in more detail.

DETAILED DESCRIPTION OF THE INVENTION

Figure 1:
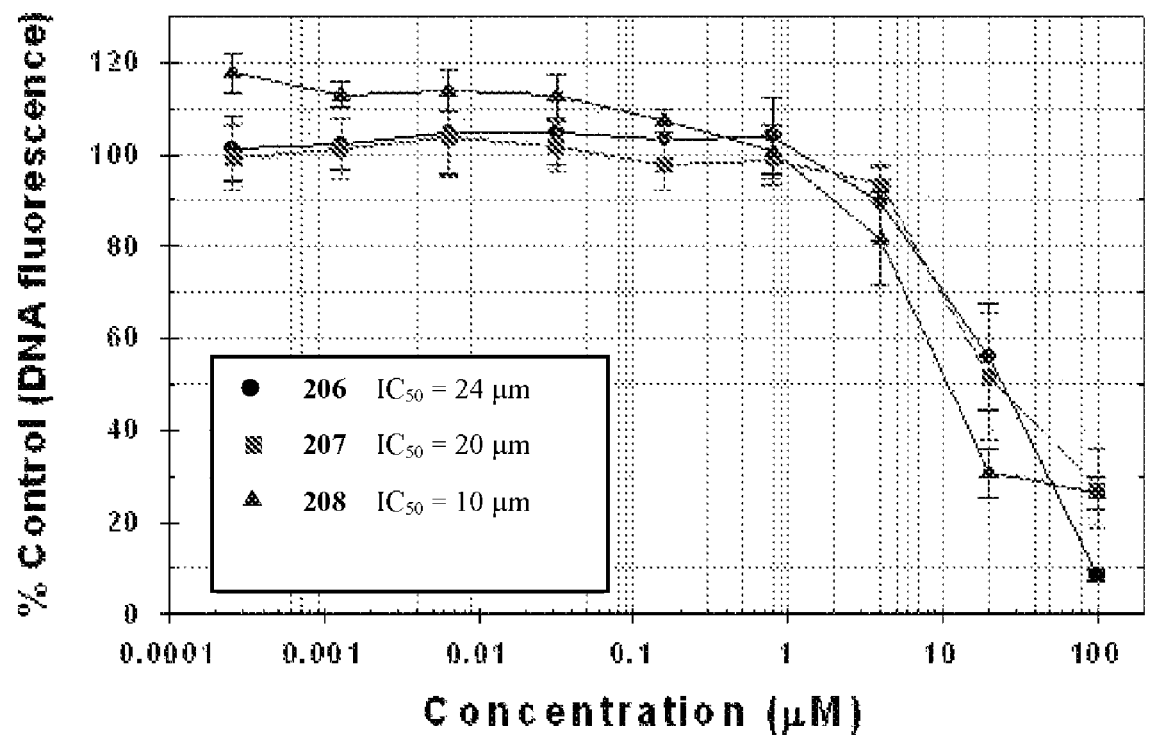
FIG. 1 illustrates the dose dependent antiproliferative effects of benzimidazole compounds 206-208 (Table 1) using PC-3 human prostate cancer cells, using the DNA assay described in Example 9.

The present invention affords compounds, compositions, and methods that are useful for treating and/or preventing cancer. In particular, certain benzimidazole molecules have been found to act as anti-proliferation agents. The subject benzimidazole compounds (1-9 and 22-27) typically are 2-substituted, with additional aryl, heteroaryl, and/or cycloalkyl substitutions at the 1- or 7-positions. Similarly, the subject imidazopyridine (10-13 and 16-19), imidazopyrazine (14 and 20), and purine (15 and 21) compounds are 2-substituted, with additional aryl, alkyl, heteroaryl, and/or cycloalkyl substitutions at the 1 positions. The synthesis of the molecules was accomplished using Microwave Assisted Organic Synthesis (MAOS), in which the desired molecules were obtained in modest yields.

Cancers that can be treated and/or prevented using the compounds disclosed herein include, but are not limited to, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreatic cancer, ovary cancer, cervical cancer, lung cancer, breast cancer, skin cancer such as squamus cell and basal cell cancers, prostate cancer, renal cell carcinoma, other known cancers that effect epithelial cells throughout the body, and fibrosis which can occur with radiation therapy. In another aspect, the compounds and methods disclosed herein can be used to treat subjects having adenomatous polyps, including those with familial adenomatous polyposis (FAP), and additionally, can be used to prevent polyps from forming in patients at risk of FAP.

In addition to the treatment of cancer, the compounds disclosed herein can be used in preparing a pharmaceutical composition for the treatment and/or prevention of inflammatory diseases. Inflammatory diseases that can be treated and/or prevented using the compounds disclosed herein include but are not limited to the group consisting of infectious disease; psoriasis; psoriatic arthritis; rheumatoid arthritis; osteoarthritis; juvenile chronic arthritis; inflammatory bowel disease (IBD); irritable bowel syndrome (IBS); ulcerative colitis; Crohn's disease; diverticulosis; pancreatitis; type I diabetes (IDDM); Graves Disease; an immune-mediated renal disease; infectious, autoimmune chronic active hepatitis; primary biliary cirrhosis; granulomatous hepatitis; sclerosing cholangitis; multiple sclerosis (MS); idiopathic demyelinating polyneuropathy; Guillain-Barre syndrome; chronic inflammatory demyelinating polyneuropathy, systemic lupus erythematosus (SLE); amyloidosis; myasthenia gravis; splenomegaly; transplant rejection; graft-versus-host disease; atherosclerosis; spondyloarthropathies; systemic sclerosis; idiopathic inflammatory myopathies; Sjogren's syndrome; systemic vasculitis; sarcoidosis; autoimmune hemolytic anemia; autoimmune thrombocytopenia; thyroiditis; gluten-sensitive enteropathy; endotoxemia; septicemia; toxic shock syndrome; a bullous skin disease; erythema multiform; atopic dermatitis; psoriasis; contact dermatitis; neutrophilic dermatoses; cystic fibrosis; allergic asthma; allergic rhinitis; food hypersensitivity; urticaria; eosinophilic pneumonia; idiopathic, pulmonary fibrosis; adult respiratory disease (ARD); acute respiratory distress syndrome (ARDS); asthma; chronic obstructive pulmonary disease (COPD); airway hyper-responsiveness; chronic bronchitis; hypersensitivity pneumonitis; septic shock; transplant rejection and graft-versus-host disease (GVHD); and multiple organ failure.

For the compounds disclosed herein, more than one reaction scheme may be provided for preparing a compound. The reaction schemes that are not specifically provided for the preparation of a stated compound are applicable for its synthesis, if the appropriate substitutions can be provided for in the precursors, starting materials, or reagents employed in that scheme.

In one aspect, this invention provides a compound having the formula:

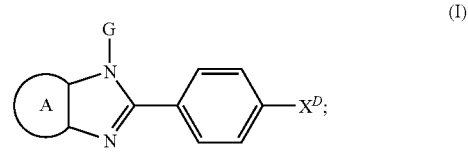

(I)

wherein

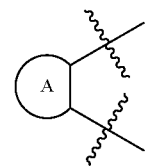

is selected from:

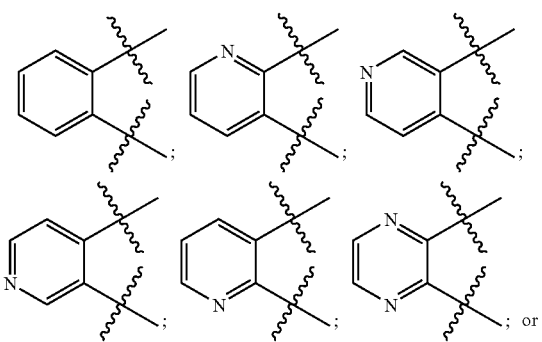

-continued

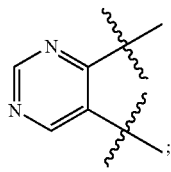

wherein G is selected from

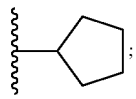 ; 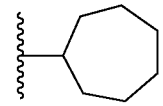 ; 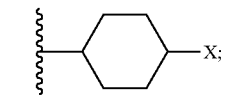 ;

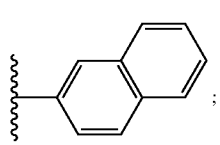 ; 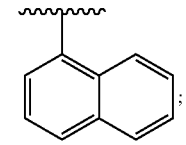 ;

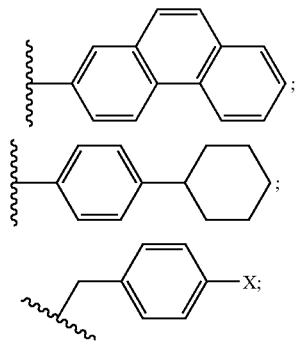 ; 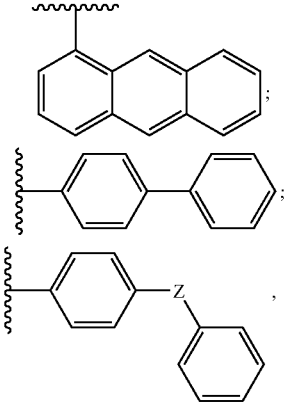 , wherein Z is selected from CH$_2$, NH, O, or S;

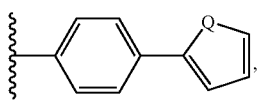 , wherein Q is selected from CH$_2$, NH, O, or S;

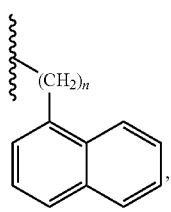 , wherein n is 0, 1, 2, or 3; or

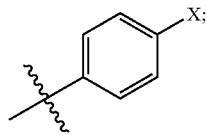

wherein X in each occurrence is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide;
wherein X$^D$ is selected from

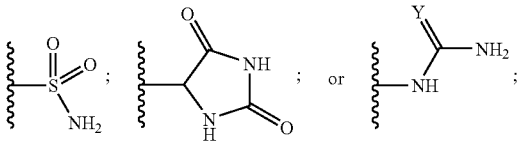

and Y is selected from O or NH.

In one aspect, the present invention provides a compound based on (I) having the formula:

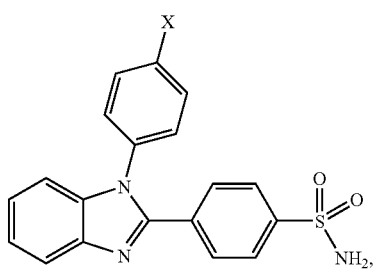

wherein Y can be selected from O or NH; and X is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide. For instance, X can be $X^A$, wherein $X^A$ is selected from H, $CH_3$, $C(CH_3)_3$, $CF_3$, $OCF_3$, $C_6H_5$, $OCH_3$, $OC(CH_3)_3$, or Cl.

Compounds having the templates according to formulas 1 and 2 may be prepared at least as exemplified in Scheme 1 provided in Example 1. Scheme 1 also is applicable to many other related aryl substituted benzimidazole compounds, with the appropriate selection of substitution in the precursors, starting materials, or reagents. While Scheme 1 presents a specific synthetic method for a compound 1 template, this scheme is also applicable to compounds having the formula 2, in which the benzoyl chloride is selected according to the desired template, Example 2. For example, compound 2 may be prepared according to Scheme 1 using the substituted benzoyl chloride

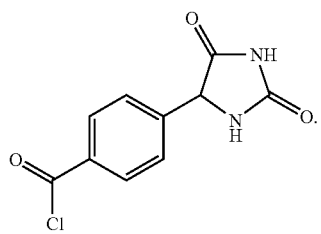

The synthesis of compounds corresponding to formula 3 can be accomplished at least as exemplified in Scheme 2 of Example 3.

An additional aspect of the invention provides compounds based on (I) having the formula:

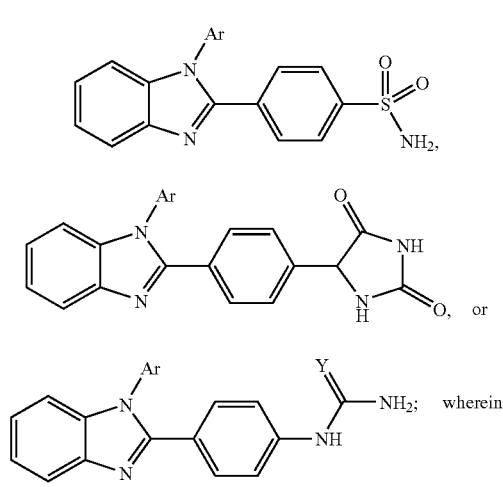

Ar can be selected from:

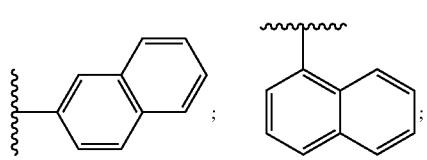

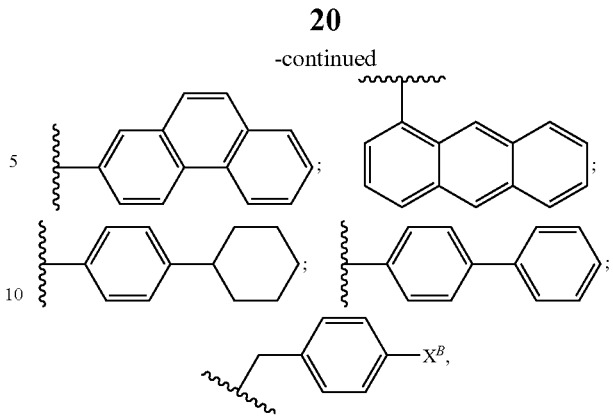

wherein $X^B$ can be $CH_3$, $C(CH_3)_3$, or $OCH_3$;

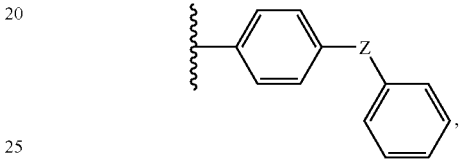

wherein Z can be $CH_2$, NH, O, or S;

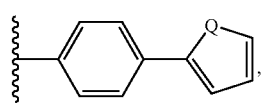

wherein Q can be $CH_2$, NH, O, or S; or

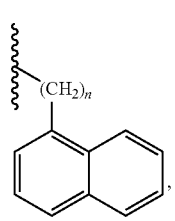

wherein n can be 0, 1, 2, or 3; and Y can be selected from O or NH. Compounds corresponding to formula 4 and 5 can be prepared in a fashion analogous to that exemplified in Scheme 1 when the appropriate aromatic amine derivative and substituted benzoyl chloride are used as in Examples 1 and 2. Compounds corresponding to formula 6 can be prepared in a fashion analogous to that exemplified in Scheme 2 when the appropriate aromatic amine derivative Example 3.

Additionally, the invention provides compounds based on (I) having the formula:

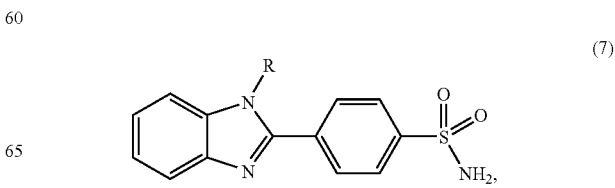

-continued

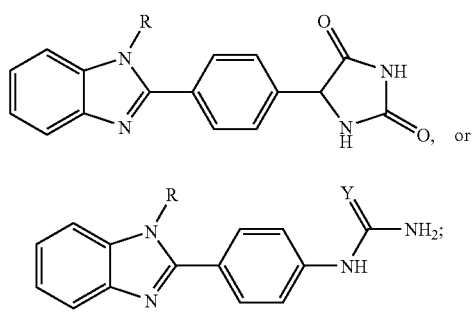
(8)

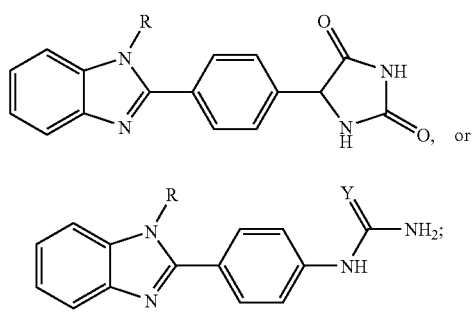
(9)

wherein R can be

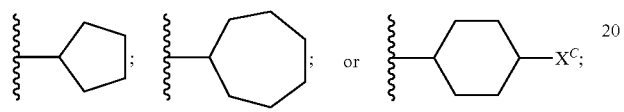

wherein $X^C$ can be H, $CH_3$, or $C(CH_3)_3$; and Y can be selected from O or NH. Compounds corresponding to formulas 7 and 8 can be prepared in a fashion at least as exemplified in Scheme 3 when the appropriate aliphatic amine derivative and substituted benzoyl chloride are used. The aliphatic amines will be substituted for compound 119 and can be selected from

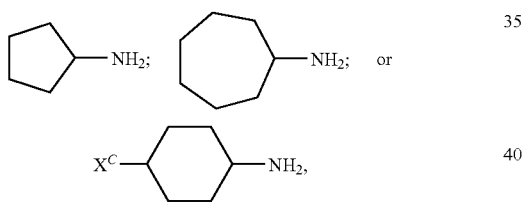

wherein $X^c$ can be H, $CH_3$, or $C(CH_3)_3$, as appropriate. Compounds corresponding to formula 9 can be prepared in a fashion at least as exemplified in Scheme 4 when the appropriate aliphatic amine derivative and substituted benzoyl chloride are used.

Yet another aspect of this invention provides for additional compounds based on (I) having the formula:

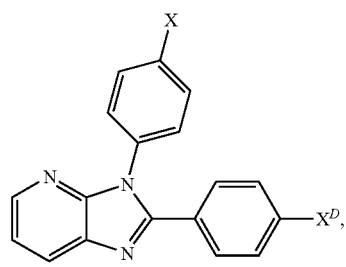
(10)

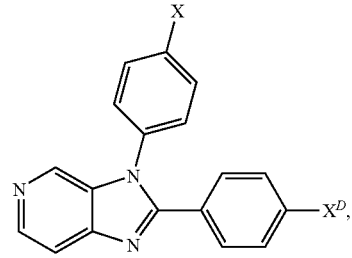
(11)

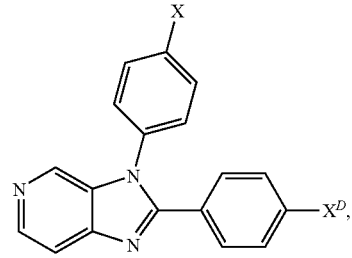
(12)

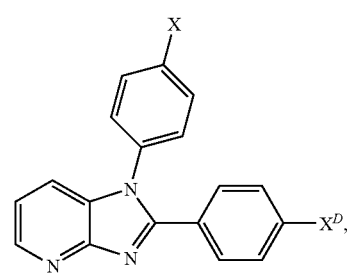
(13)

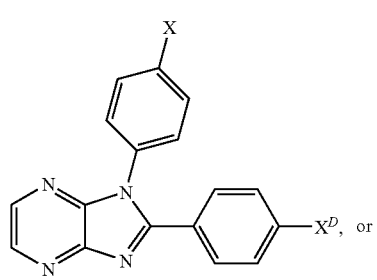
(14)

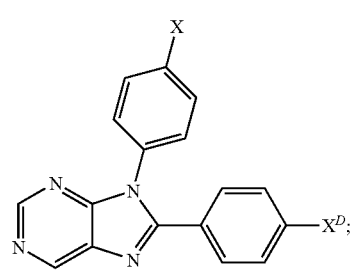
(15)

wherein X is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide; and $X^D$ can be

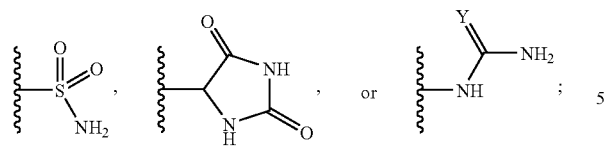 ;

and wherein Y can be selected from O or NH. For instance, X can be $X^A$, wherein $X^A$ is selected from H, $CH_3$, $C(CH_3)_3$, $CF_3$, $OCF_3$, $C_6H_5$, $OCH_3$, $OC(CH_3)_3$, or Cl.

Scheme 5 can be applied towards the synthesis of compounds of formulas 10-13 when $X^D$ is

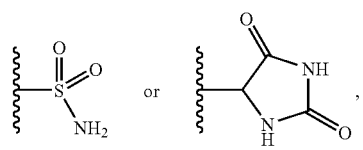

using the appropriate halogen substituted nitro pyridine

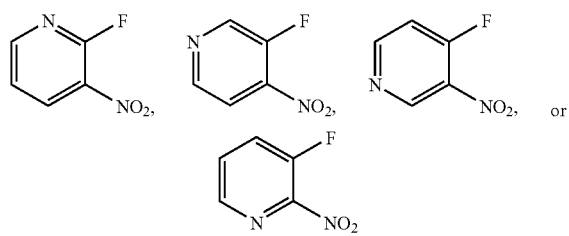

and substituted benzoyl chloride. Likewise, compounds of formulas 14 or 15 when $X^D$ is

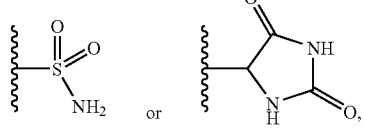

can be synthesized according to Scheme 5 using the reagent

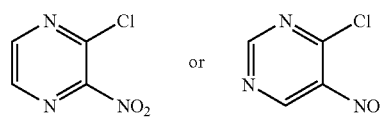

respectively and the appropriate substituted benzoyl chloride.

Scheme 6 can be applied for the preparation of compounds of the formulas 10-13 having the disclosed X substituents and wherein $X^D$ is

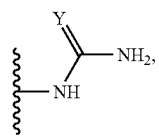

wherein Y can be NH or O, using the appropriate halogen substituted nitro pyridine. Likewise, compounds of the formulas 14 or 15 having the disclosed X substituents and wherein $X^D$ is

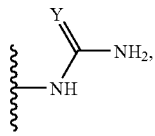

wherein Y can be NH or O, can be synthesized according to Scheme 6 using the reagents

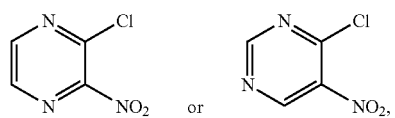

respectively.

Further, this invention also provides a compound based on (I) having the formula:

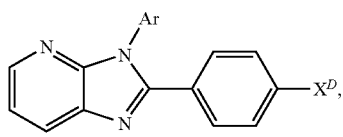 (16)

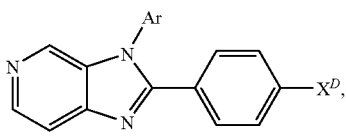 (17)

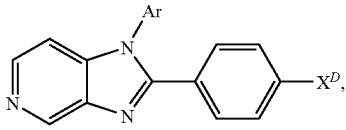 (18)

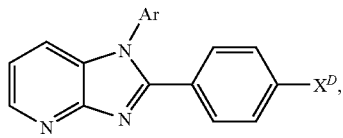 (19)

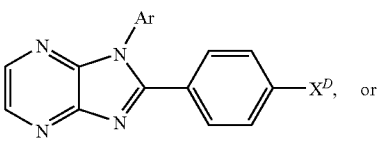 (20)

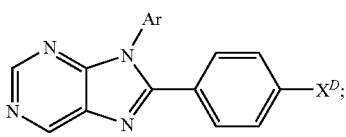 (21)

wherein Ar can be selected from

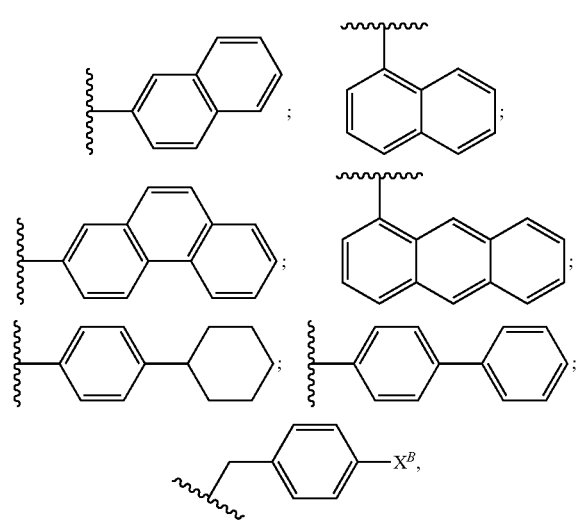

wherein $X^B$ can be $CH_3$, $C(CH_3)_3$, or $OCH_3$;

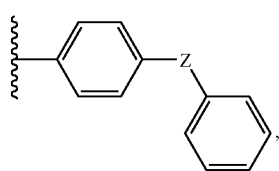

wherein Z can be $CH_2$, NH, O, or S;

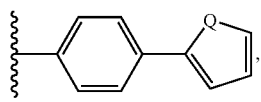

wherein Q can be $CH_2$, NH, O, or S; or

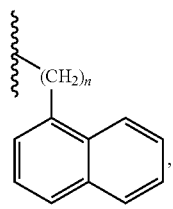

wherein n can be 0, 1, 2, or 3; $X^D$ can be selected from

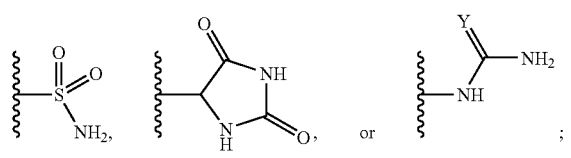

and wherein Y can be selected from O or NH.

Scheme 5 can be applied towards the synthesis of molecules following the formula 16-19 when $X^D$ is

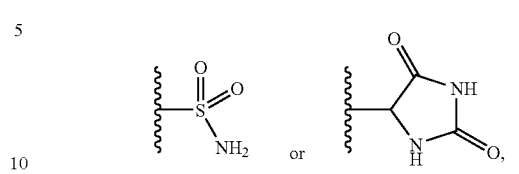

using the appropriate substituted benzoyl chloride and one of the following halogen substituted nitro pyridines:

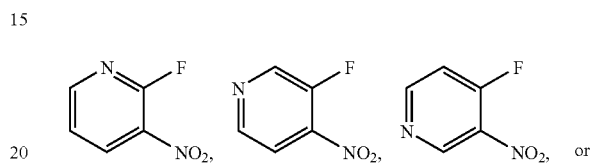

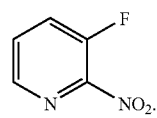

Likewise, compounds following the formula 20 or 21 when $X^D$ is

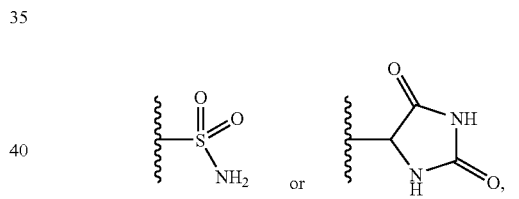

can be synthesized according to Scheme 5 using the reagents

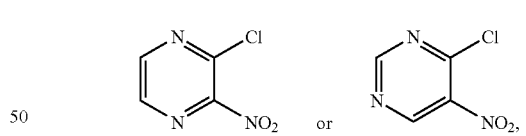

respectively, and the appropriately substituted benzoyl chloride.

Scheme 6 can be applied for the preparation of compounds following the formula 16-19 having the disclosed X substituents and wherein $X^D$ is

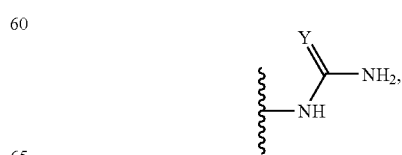

wherein Y can be NH or O, using the appropriate halogen substituted nitro pyridine. Likewise, compounds following the formula 20 or 21 having the disclosed X substituents and wherein $X^D$ is

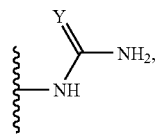

wherein Y can be NH or O, can be synthesized according to Scheme 6 using the reagents

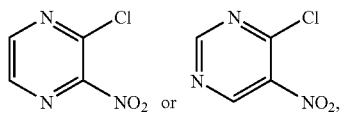

respectively.

In another aspect, this invention provides a compound of the formula:

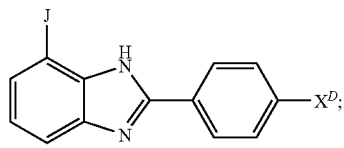

(II)

wherein J is selected from

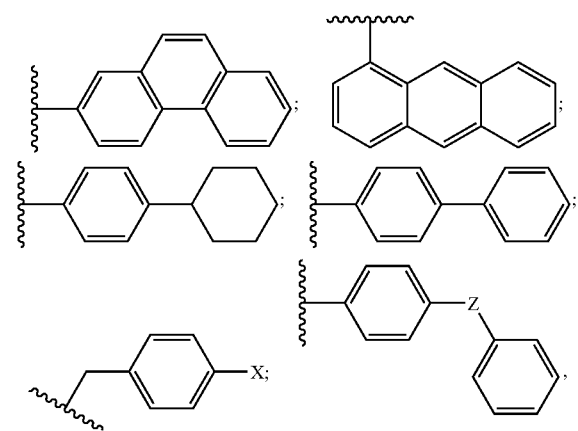

wherein Z is selected from $CH_2$, NH, O, or S;

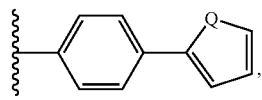

wherein Q is selected from $CH_2$, NH, O, or S;

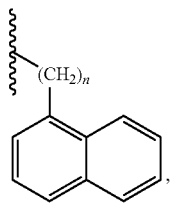

wherein n is 0, 1, 2, or 3; or

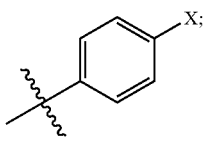

wherein X in each occurrence is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide;

wherein $X^D$ is selected from

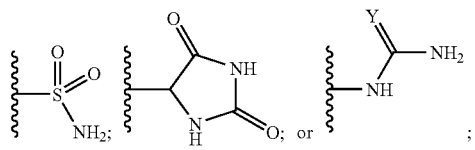

and Y is selected from O or NH.

A further aspect of this invention provides for a compound based on (II) having the formula:

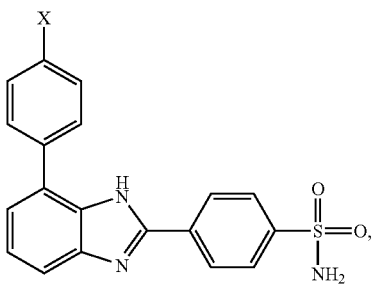

(22)

-continued (23)

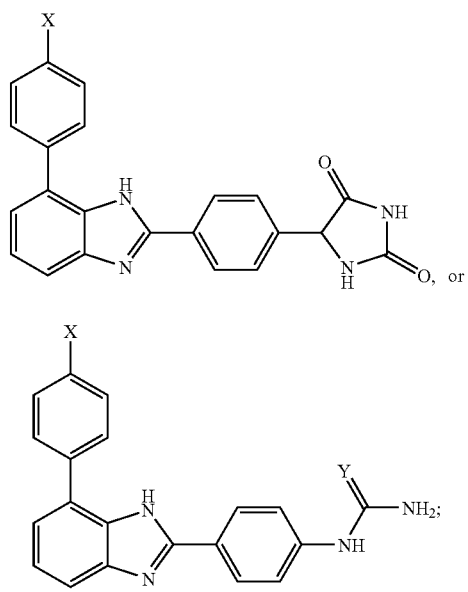

(24)

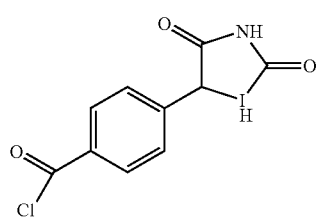

wherein Y can be selected from O or NH; and X is selected from hydrogen; a halide (F, Cl, Br, or I); a linear or branched alkyl having up to 10 carbon atoms, optionally substituted with at least one halide; or an alkoxide having a linear or branched alkyl group having up to 10 carbon atoms, optionally substituted with at least one halide. For instance, X can be $X^A$, wherein $X^A$ is selected from H, $CH_3$, $C(CH_3)_3$, $CF_3$, $OCF_3$, $C_6H_5$, $OCH_3$, $OC(CH_3)_3$, or Cl. Compounds of formulas 22-23 may be prepared at least according to Scheme 7, provided in Example 14. The synthesis of 22 is illustrated in Scheme 7 as shown. The synthesis of 23 may be achieved by using the reagent

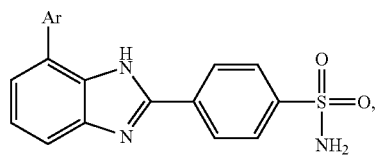

in lieu of 113. Compounds of formula 24 may be prepared at least according to Scheme 9 using the appropriate reagents based on the substituents as required in the final compound.

A further aspect of this invention provides for a compound based on (II) having the formula:

(25)

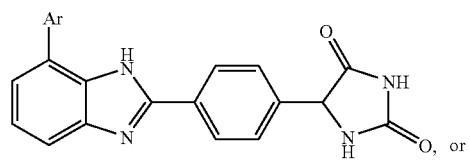

-continued (26)

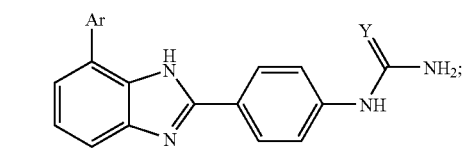

(27)

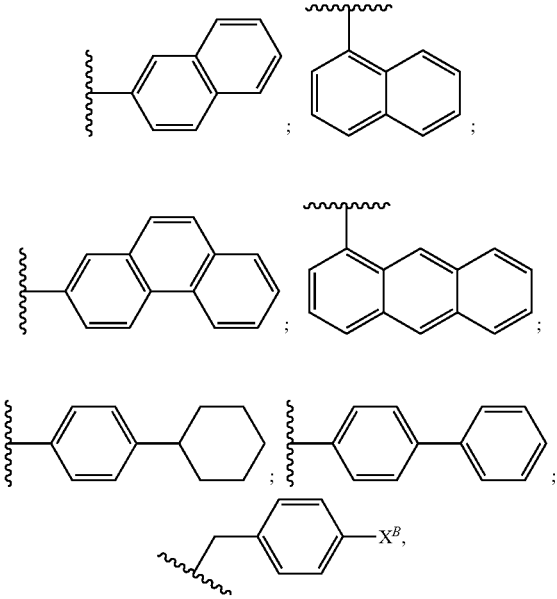

wherein Ar can be selected from

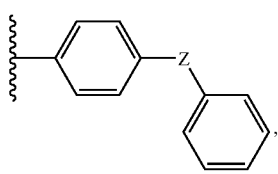

wherein $X^B$ can be $CH_3$, $C(CH_3)_3$, or $OCH_3$;

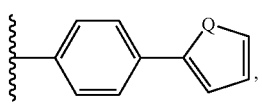

wherein Z can be $CH_2$, NH, O, or S;

wherein Q can be CH$_2$, NH, O, or S; or

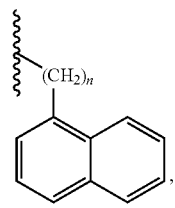

wherein n can be 0, 1, 2, or 3; and Y can be selected from O or NH. Compounds of formulas 25-26 may be prepared at least according to Scheme 7 using the appropriate Grignard reagent and substituted benzoyl chloride, provided in Example 14. Compounds of formula 27 may be prepared at least according to Scheme 9 using the appropriate Grignard reagent.

In a particular aspect of formula 1, wherein X is —CH$_3$, the benzimidazole derivative is 4-(1-p-tolyl-1H-benzo[d]imidazol-2-yl)benzenesulfonamide—a compound having the chemical structure:

(206)

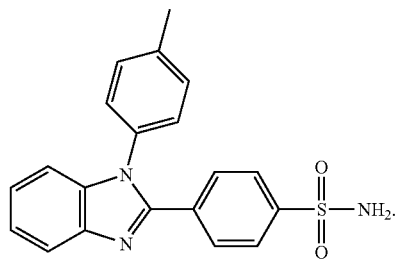

In yet another particular aspect of formula 1, wherein X is —C(CH$_3$)$_3$, the benzimidazole derivative is 4-(1-(4-tert-butylphenyl)-1H-benzo[d]imidazol-2-yl)benzenesulfonamide—a compound having the chemical structure:

(207)

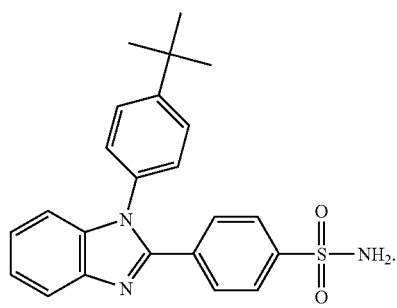

In a particular aspect of formula 4, wherein —Ar is

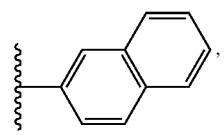

the benzimidazole derivative is 4-(1-(naphthalen-2-yl)-1H-benzo[d]imidazol-2-yl)benzenesulfonamide—a compound having the chemical structure:

(208)

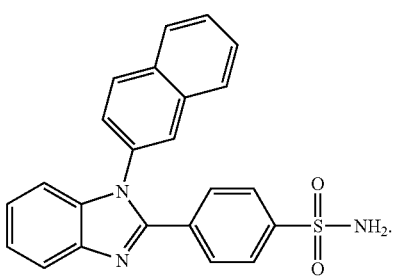

In another particular aspect of formula 4, wherein —Ar is

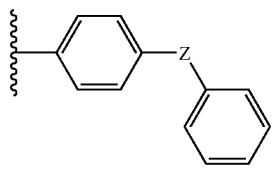

and Z is —CH$_2$—, the benzimidazole derivative is 4-(1-(4-benzylphenyl)-1H-benzo[d]imidazol-2-yl)benzenesulfonamide, a compound having the chemical structure:

(209)

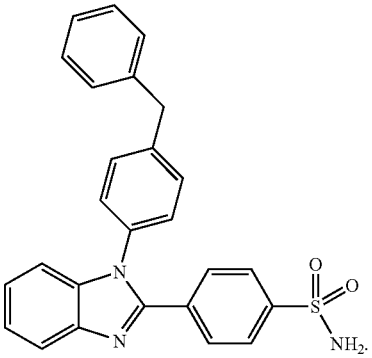

In yet another particular aspect of formula 4, wherein —Ar is

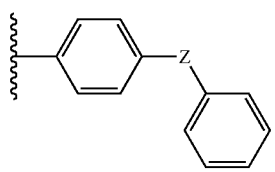

and Z is O, the benzimidazole derivative is 4-(1-(4-phenoxyphenyl)-1H-benzo[d]imidazol-2-yl)benzenesulfonamide, a compound having the chemical structure:

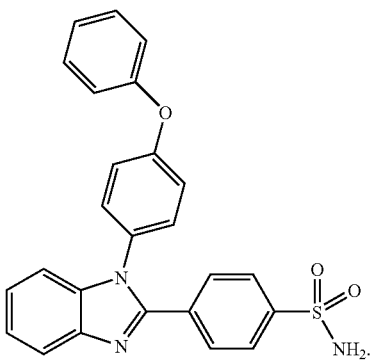

(210)

In yet another particular aspect of formula 4, wherein —Ar is

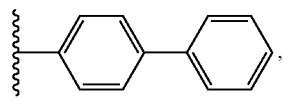, the benzimidazole derivative is 4-(1-(biphenyl-4-yl)-1H-benzo[d]imidazol-2-yl)benzenesulfonamide, a compound having the chemical formula:

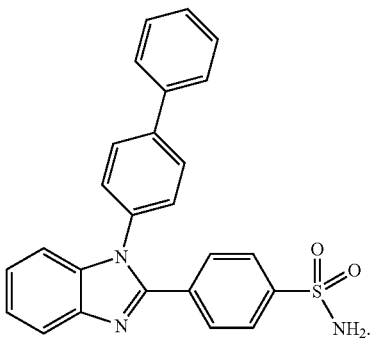

(211)

The PDK1/Akt mechanism is a component in the development and progression of prostate cancer. PDK1 is over-expressed in a number of tumor cells and the inhibition of PDK1 kinase has been linked to the induction of mitochondrial-mediated apoptosis and decreased proliferation in the PC-3 human prostate cancer cell line. Therefore, due to its role in cancer and the regulation of cell cycle, PDK1 is an excellent target for development of chemotherapeutic agents for prostate cancer. While not intending to be bound by theory, one aspect of this invention includes the evaluation of the three-dimensional steric and electronic features of the potential binding interactions of proposed or test molecules, for example, when docked in the ATP binding pocket of PDK1. Again, while not bound by theory, useful pharmacophores that are disclosed herein may have some of the following properties: large hydrophobic substituents, which in various aspects may include aromatic or cycloaliphatic substituents; at least one hydrogen bonding substituent; a heteroaromatic central ring; and small hydrophobic substituents In one aspect, for example, in characterizing the structure-activity of celecoxib analogs or derivatives, it was found that useful compounds contained aromatic hydrophobic groups. Again, while not intending to be bound by theory, it is believed that a so-called "fuzzy" pharmacophore, which roughly describes very delocalized potential pi-pi ($\pi$-$\pi$) interactions involving the protein and an aromatic group, may be useful. For example, such an interaction in which a phenanthrene group of a celecoxib analog is docked in the aromatic rich ATP binding pocket of PDK1 appears to afford stable conformations.

In a further aspect, useful pharmacophores of this invention that have the ability to inhibit PDK1 kinase activity and proliferation in PC-3 cells can have particular relationships between their electronic and size and/or shape features their. In this aspect, for example, useful pharmacophores can have size to lipophilicity ratios, calculated by the ratio of molar volume (in cm$^3$/mol) to lipophilicity (as c Log P) ratios in the range from about 50 to about 90. In another aspect, useful pharmacophores can have size to lipophilicity ratios in the range from about 60 to about 85, or from about 65 to about 80. For example, compounds 206-208 of Table 1 have ratios of molar volume (in cm$^3$/mol) to lipophilicity (as c Log P) of 78, 69, and 67, respectively.

TABLE 1

Activity of Benzimidazole Compounds and Comparative Molecules for the Inhibition of PC-3 Cells.

| No. | COMPOUND | PC3 IC$_{50}$ (μM) | MOLAR VOLUME (cm$^3$/mol) | cLogP |
|---|---|---|---|---|
| 201 | Celecoxib | 30 | 284 | 3.41 |

TABLE 1-continued
Activity of Benzimidazole Compounds and Comparative Molecules for the Inhibition of PC-3 Cells.
| No. | COMPOUND | PC3 IC$_{50}$ ($\mu$M) | MOLAR VOLUME (cm$^3$/mol) | cLogP |
|---|---|---|---|---|
| 202 | 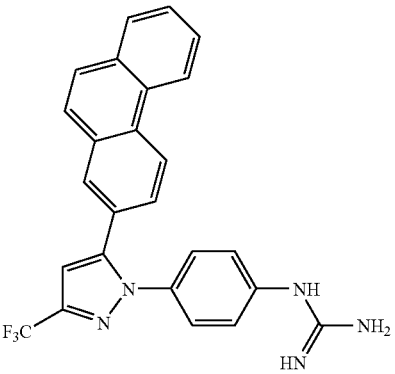<br>OSU-03013 | 3 | 333 | 5.17 |
| 203 | 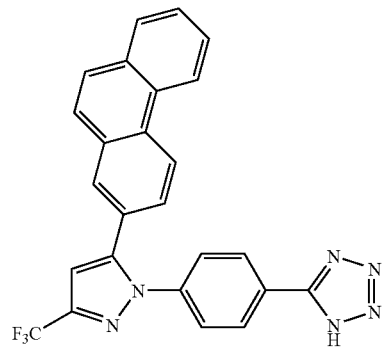 | 32 | 312 | 5.31 |
| 204 | 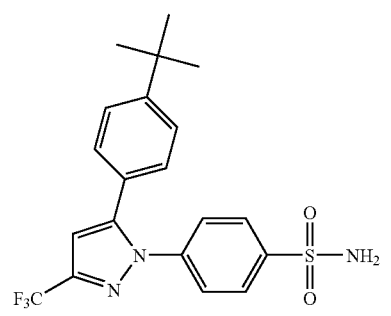 | 18 | 309 | 4.7 |
| 205 | 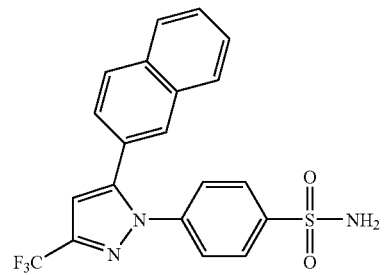 | 10 | 298 | 4.14 |

TABLE 1-continued

Activity of Benzimidazole Compounds and
Comparative Molecules for the Inhibition of PC-3 Cells.

| No. | COMPOUND | PC3 IC$_{50}$ (μM) | MOLAR VOLUME (cm$^3$/mol) | cLogP |
|---|---|---|---|---|
| 206 | | 24 | 287 | 3.66 |
| 207 | | 20 | 350 | 5.08 |
| 208 | | 10 | 301 | 4.49 |

In addition to evaluating the activity of the inventive benzimidazole, purine, imidazopyridine, and imidazopyrizine compounds for the inhibition of PC-3 cells, a number of other methods for biological testing may be used for the inventive compounds. For example, other models and tests that can be used include, but are not limited to, the Murine Lewis lung Carcinoma Model, Human prostate cancer cell tumors, LNCaP, and the following cell lines and growth studies.

Cell lines that can be used include, but are not limited to, classic small cell lung cancer (SCLC) cell lines NCI-H209, NCI-H345, and NCI-H510; variant SCLC cell lines NCI-N417 and NCI-H82; large cell carcinoma cell line NCI-H1155; adeno carcinoma cell line NCI-H23; and bronchioalveolar carcinoma cell line A549, breast cancer cell line MCF-7 (American Type Tissue Culture Rockville Md.; ATCC) and colon cancer cell lines such as NCI-H630 (ATCC), HT 29, SW948, HCA-7; prostate cancer cell lines PC3, LNCap, MDA Pca 2a, MDA Pca 2b; and others that can be tested in vivo or in vitro. Growth studies that can be used include, but are not limited to, a modification (Promega Cell-Titer 96®, Promega Madison, Wis.) of the semiautomated colorimetric assay, MTT (Nakanishi, et al. *Exper. Cell Biol.* 1988, 56, 74-85), which quantifies cell numbers based on reduction of a tetrazolium compound by tumor cells as determined by a spectrophotometer (540 nm) is used. Other tumor models that can be used are disclosed in U.S. Pat. No. 6,469, 040 and those defined the Developmental Therapeutics Program NCI/NIH (dtp.nci.nih.gov/index.html), the entirety of which is incorporated herein by reference in its entirety.

Other potential cell lines include, but are not limited to, the following: Leukemia cell lines P388, P388/ADR, CCRF-CEM, HL-60(TB), K-562, MOLT-4, RPMI-8226, and SR; non-small cell lung cell lines LXFL 529, A549/ATCC, EKVX, HOP-62, HOP-92, NCI-H226, NCI-H23, NCI-H322M, NCI-H460, and NCI-H522; colon cell lines DLD-1, KM20L2, COLO 205, HCC-2998, HCT-116, HCT-15, HT29, KM12, and SW-620; CNS cell lines SNB-78, XF 498, SF-268, SF-295, SF-539, SNB-19, SNB-75, and U251; melanoma cell lines RPMI-7951, M19-MEL, LOX IMVI, MALME-3M, M14, MDA-MB-435, SK-MEL-2, SK-MEL-28, SK-MEL-5, UACC-257, and UACC-62; ovarian cell lines IGR-OV1, OVCAR-3, OVCAR-4, OVCAR-5, OVCAR-8, NCI/ADR-RES, and SK-OV-3; renal cell lines RXF-631, SN12K1, 786-0, A498, ACHN, CAKI-1, RXF 393, SN12C, TK-10, and UO-31; prostate cancer cell lines PC-3 and DU-145; breast cancer cell lines MDA-MB-468, MCF7, MDA-MB-231/ATCC, HS 578T, MDA-N, BT-549, and T-47D; small cell lung cell lines DMS 114 and SHP-77.

The benzimidazole, purine, imidazopyridine, and imidazopyrizine compounds provided herein may be administered by any suitable route known to those skilled in the art, preferably in the form of a pharmaceutical composition adapted to such a route, and in a dose effective for the treatment intended. The active compounds and composition may, for example, be administered orally, intravascularly, intraperitoneally, intranasal, intrabronchial, subcutaneously, intramuscularly or topically (including aerosol). The administration of the present invention may be for either prevention or treatment purposes. The methods and compositions used herein may be used alone or in conjunction with additional therapies known to those skilled in the art in the prevention or treatment of neoplasia. Alternatively, the methods and compositions described herein may be used as conjunctive therapy. By way of example, the anti-neoplastic agents disclosed herein may be administered alone or in conjunction with other anti-neoplastic agents, cyclooxygenase-2 inhibitors, other growth inhibiting agents, or other drugs or nutrients.

As used herein, the phrase "conjunctive therapy" (or "combination therapy"), in defining the use of an anti-neoplastic agent disclosed herein and another pharmaceutical agent, is intended to encompass administration of each agent in a sequential manner in a regimen that will provide beneficial effects of the drug combination, and is intended as well to encompass co-administration of these agents in a substantially simultaneous manner, such as in a single formulation having a fixed ratio of these active agents, or in multiple, separate formulations for each agent. In another aspect, the present invention also provides for a pharmaceutical composition comprising a therapeutically-effective amount of at least one compound according to the present disclosure, or a pharmaceutically-acceptable salt thereof, in association with at least one pharmaceutically-acceptable carrier. This composition may also comprise other pharmaceutically-acceptable excipients, stabilizers, diluents, adjuvants, preservatives, binders, coatings, disintegrants, sorbants, or other suitable additives or components as understood by one of ordinary skill in the art.

For oral administration, the pharmaceutical composition may be in the form of, for example, a tablet, a capsule, a suspension, a powder, a liquid, or a solution or any other suitable form. The pharmaceutical composition can be made in the form of a dosage unit containing a particular amount of the active ingredient(s). Examples of such dosage units are capsules, tablets, powders, granules, or suspensions, with conventional additives such as lactose, mannitol, corn or potato starch, and the like; with binders such as crystalline or microcrystalline cellulose, cellulose derivatives, acacia, corn starch, or gelatins; with disintegrators such as corn starch, potato starch, or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, a compound of this invention may be combined with a sterile aqueous solution that can be isotonic with the blood of the recipient. Such formulations may be prepared, for example, by dissolving or suspending a solid active ingredient, which can be a neutral compound or a salt, in water containing physiologically compatible substances such as sodium chloride, glycine, and the like. Such a solution or suspension could have a buffered pH compatible with physiological conditions to produce an aqueous solution or suspension that could be rendered sterile. The formulations may be present in unit or multi-dose containers such as sealed ampoules or vials.

If the neoplasia is localized in the G.I. tract, the compound may be formulated with acid-stable, base-labile coatings known to one of skill in the art which begin to dissolve in the high pH small intestine. Formulations to enhance local pharmacologic effects and reduce systemic uptake are typical.

Formulations suitable for parenteral administration typically can comprise a sterile aqueous preparation of the active compound which is usually made isotonic. Preparations for injections may also be formulated by suspending or emulsifying the compounds in non-aqueous solvent, such as vegetable oil, synthetic aliphatic acid glycerides, esters of higher aliphatic acids, propylene glycol, or other suitable substances.

Formulations for topical use include gels, creams, oils, and the like, known to one of ordinary skill in the art. For example, aerosol delivery compositions could be prepared by formulating the compounds with known aerosol excipients, such as saline, and administered the formulation using commercially available nebulizers. Formulation in a fatty acid source may be used to enhance biocompatibility. For example, aerosol delivery is a typical method of delivery for epithelial neoplasias of the lung for prevention application.

For rectal administration, the active ingredient may be formulated into suppositories using bases which are solid at room temperature and melt or dissolve at body temperature. For example, commonly used bases include cocoa butter, glycerinated gelatin, hydrogenated vegetable oil, polyethylene glycols of various molecular weights, and fatty esters of polyethylene stearate.

The dosage form and amount can be readily established by reference to known neoplasia treatments or prophylactic regiments. For example, the amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed. The amount and dosage regimen of therapeutically active compound also can depend on the location of the neoplasia, as well as the pharmacokinetic properties of the individual treated, and thus may vary widely. Such dosage generally will be lower if the compounds are administered locally rather than systemically, and for prevention rather than for treatment. Such treatments may be administered as often as necessary and for the period of time judged necessary by the treating physician.

One of skill in the art will appreciate that the dosage regime or therapeutically effective amount of the inhibitor to be administrated may need to be optimized for each individual. The pharmaceutical compositions may contain active ingredient in the range of, for example, from about 0.1 to about 2000 mg, or in the range from about 0.5 to about 500 mg, or from about 1 to about 200 mg, though these amounts are not considered limiting. A daily dose from about 0.01 to about 100 mg/kg body weight is typical, which also can be from about 0.1 to about 50 mg/kg body weight, or from about 1 to about 30 mg/kg, which may be appropriate. The daily dose can be administered in one to four or more doses per day.

Although any methods, devices, and materials similar or equivalent to those described herein can be used in the practice or testing of the invention, the typical methods, devices and materials are herein described. All publications and patents mentioned in the disclosure of this invention are incorporated herein by reference in their entireties, for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention. Moreover, it is also to be understood that the terminology used herein is for the purpose of describing particular aspects or embodiments and is not intended to be limiting. Should the usage or terminology used in any reference that is incorporated by reference conflict with the usage or terminology used in this disclosure, the usage and terminology of this disclosure controls.

For any particular compound disclosed herein, any general structure presented also encompasses all conformational isomers, regioisomers, and stereoisomers that may arise from a particular set of substituents. Thus, the general structure also encompasses all enantiomers, diastereomers, and other optical isomers whether in enantiomeric or racemic forms, as well as mixtures of stereoisomers, as the context requires.

Also unless indicated otherwise, when a range of any type is disclosed or claimed, for example a range of molecular weights, molar volumes, c Log P, concentrations, temperatures, and the like, it is intended to disclose or claim individually each possible number that such a range could reasonably encompass, including any sub-ranges encompassed therein. For example, when the Applicants disclose or claim a chemical moiety having a certain number of atoms, for example carbon atoms, Applicants' intent is to disclose or claim individually every possible number that such a range could encompass, consistent with the disclosure herein. Thus, by the disclosure that an alkyl substituent or group can have from 1 to 10 carbon atoms or "up to" 10 carbon atoms, Applicants intent is to recite that the alkyl group have 1, 2, 3, 4, 5, 6, 7, 8, 9, or 10 carbon atoms, including any ranges, sub-ranges, or combinations thereof between any number of carbon atoms recited herein. In another example, by the disclosure that the ratio of molar volume (in cm$^3$/mol) to lipophilicity (as c Log P) is in the range from about 65 to about 80, Applicants intent is to recite individually that the ratio can be about 65, about 66, about 67, about 68, about 69, about 70, about 71, about 72, about 73, about 74, or about 75, including any ranges, sub-ranges, or combinations thereof, between any of these ratios. Accordingly, Applicants reserve the right to proviso out or exclude any individual members of such a group, including any sub-ranges or combinations of sub-ranges within the group, that can be claimed according to a range or in any similar manner, if for any reason Applicants choose to claim less than the full measure of the disclosure, for example, to account for a reference that Applicants are unaware of at the time of the filing of the application.

All publications and patents mentioned in this disclosure are incorporated herein by reference in their entireties, for the purpose of describing and disclosing, for example, the constructs and methodologies that are described in the publications, which might be used in connection with the presently described methods, compositions, articles, and processes. The publications discussed throughout the text are provided solely for their disclosure prior to the filing date of the present application. Nothing herein is to be construed as an admission that the inventors are not entitled to antedate such disclosure by virtue of prior invention. Should the usage or terminology used in any reference that is incorporated by reference conflict with the usage or terminology used in this disclosure, the usage and terminology of this disclosure controls. The Abstract of the disclosure is provided to satisfy the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." The Abstract is not intended to be used to construe the scope of the appended claims or to limit the scope of the subject matter disclosed herein. Moreover, any headings are not intended to be used to construe the scope of the appended claims or to limit the scope of the subject matter disclosed herein. Any use of the past tense to describe an example otherwise indicated as constructive or prophetic is not intended to reflect that the constructive or prophetic example has actually been carried out.

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

In the following examples, unless otherwise specified, the syntheses and preparations described therein were carried out under an inert atmosphere such as nitrogen or argon. Solvents were purchased from commercial sources and were typically dried prior to use. Unless otherwise specified, reagents were obtained from commercial sources.

EXAMPLES

Example 1

Synthesis of Aromatic-Substituted Benzimidazole Compounds of Formula 1

The preparation of aromatic-substituted benzimidazole analogs was accomplished using the synthetic route outlined in Scheme 1. Under microwave irradiation, a 4-substituted aniline derivative 110 was coupled to 1-fluoro-2-nitrobenzene 109 to give a nitro diaryl amine 111. Using a domestic microwave, the reaction produced yields greater than 99.5% when the aniline substituent was an electron donating group. (See: Xu, Z.; Lu, Y.; Guo, Z-R. *Synlett* 2003, 564-566.) However, optimizing the reaction conditions was difficult using a standard household microwave and relied heavily on the placement of the vessel in the microwave cavity to ensure reproducibility.

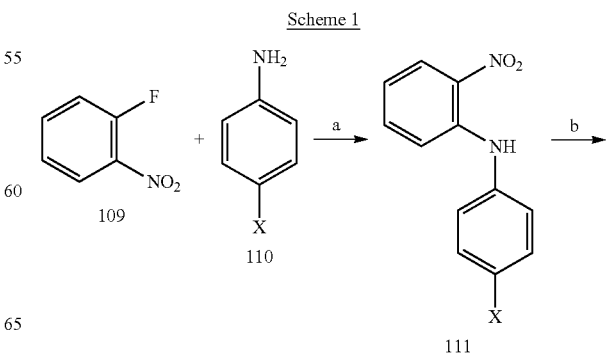

Scheme 1

-continued

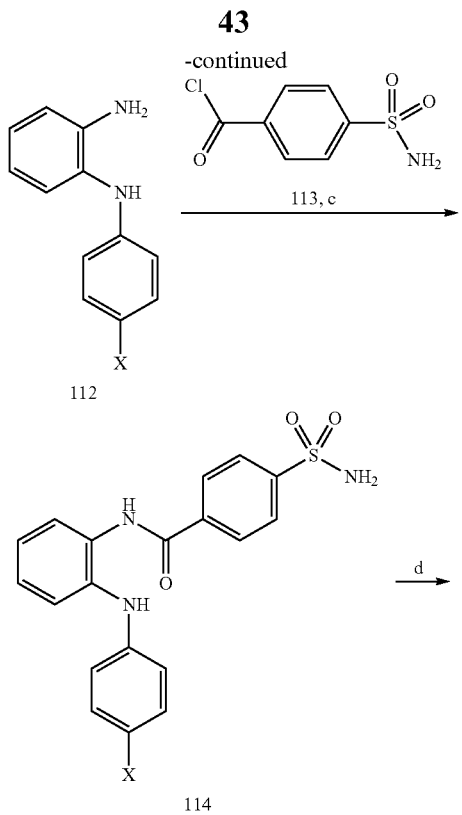

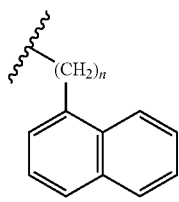

where n is 0, 1, 2, or 3; or other analogs disclosed herein can be generated in a similar fashion as illustrated in Scheme 1, with the selection of an appropriate analog of compound 110 in the reaction scheme. The resulting compounds were or could be characterized by NMR spectroscopy, IR spectroscopy, melting point, and mass spectrometry. Among other ways, the benzoyl chloride 113 may be obtained by the reaction of the corresponding $SO_2NH_2$-substituted benzoic acid with $SOCl_2$, to obtain the desired benzoyl chloride 113.

Example 2

Synthesis of Aromatic-Substituted Benzimidazole Compounds of Formula 2

Compounds of the formula

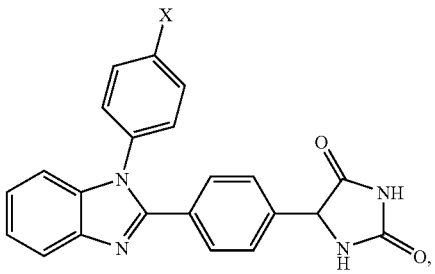

(2)

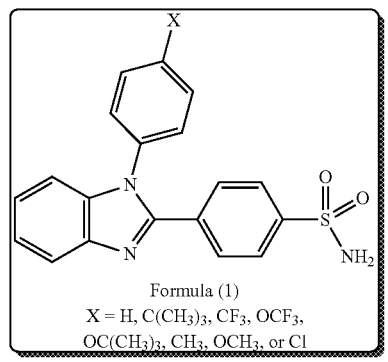

When the reaction was conducted in the CEM Discovery System, a single mode industrial microwave able to maintain the temperature and pressure of the reaction mixture, the reaction time was decreased from 20 minutes to 5 minutes in some cases. The CEM reaction gave reproducible results and the crude reaction mixture showed no evidence of side products. The nitro group of the diaryl amine was reduced using zinc and ammonium chloride. After about 24 hours, approximately 90-100% of the nitro compound 111 was reduced to the diamine 112. Ring formation was afforded from a condensation reaction of the diamine and the benzoyl chloride 113 in two steps to give the target molecules of formula 1. For general information, see: Goker, H., et al., *Bioorganic. Medicinal Chemistry* 2002, 10, 2589-2596. The compounds corresponding to formula 4 wherein Ar is 1-napthylenyl; 2-napthylenyl; phenanthrenyl; anthracenyl, can be prepared according to Scheme 1, using the benzoyl chloride

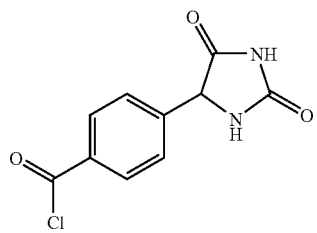

for preparing the compounds. The substituents X, are defined herein. The compounds of formula 5 wherein Ar is 1-napthylenyl; 2-napthylenyl; phenanthrenyl; anthracenyl,

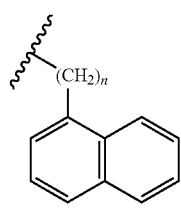

wherein n is 0, 1, 2, or 3; or other analogs disclosed herein can be generated in a similar fashion as illustrated in Scheme 1, with the selection of an appropriate analog of compound 110 in the reaction scheme.

Hydantoin substituted benzoic acid can be treated with thionyl chloride to prepare

Example 3

Synthesis of Aromatic-Substituted Benzimidazole Compounds of Formula 3

The preparation of aromatic-substituted benzimidazole compounds of formula 3 was accomplished using the synthetic route outlined in Scheme 2. Under microwave irradiation, a 4-substituted aniline derivative 110 was coupled to 1-fluoro-2-nitrobenzene 109 to give a nitro diaryl amine 111 as previously described. The diaryl amine 111 can be reduced to the diamine 112. Subsequently, the diamine can be reacted with nitro substituted benzoic acid 115 to prepare the benzimidazole 117. The reduced molecule 118 can be converted to the desired guanidine and carbamide substituted benzimidazole. The resulting molecules were or could be purified using a combination of flash chromatography and/or recrystallization. The resulting compounds were or could be characterized by NMR spectroscopy, IR spectroscopy, melting point, and mass spectrometry.

Scheme 2

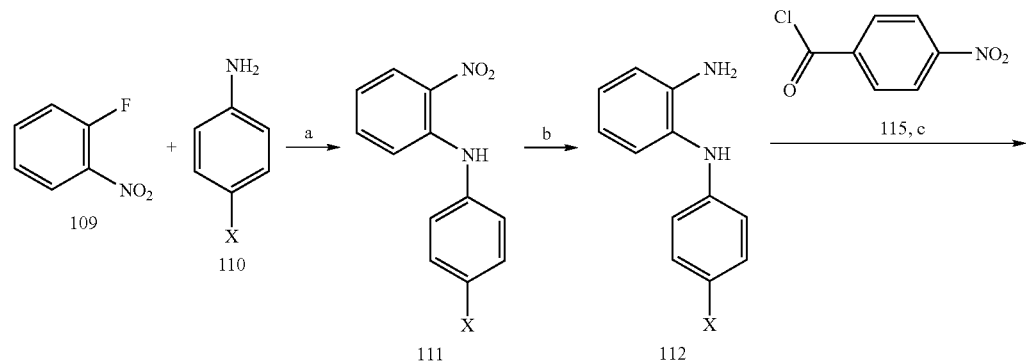

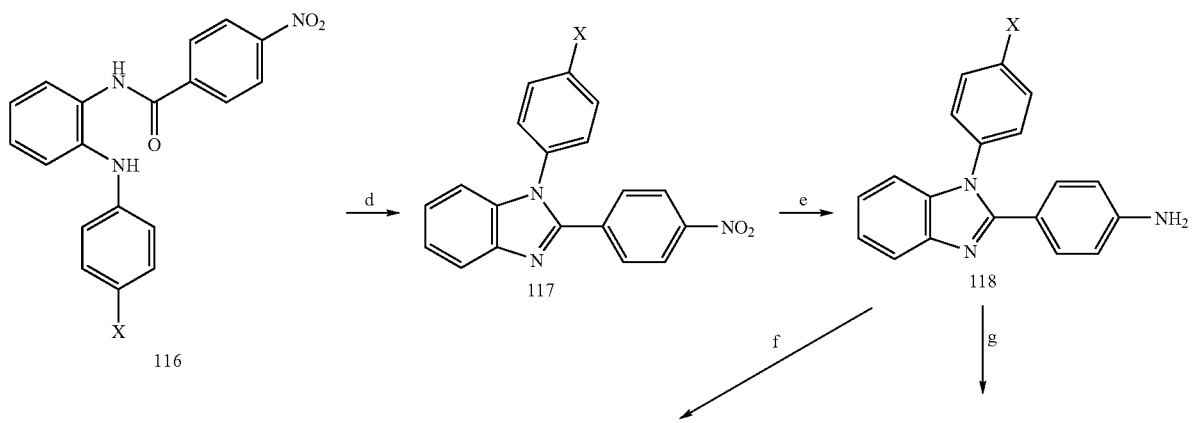

-continued

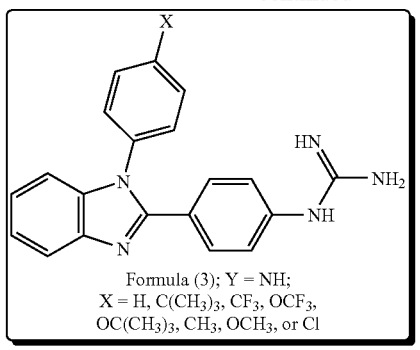

Formula (3); Y = NH;
X = H, C(CH₃)₃, CF₃, OCF₃, OC(CH₃)₃, CH₃, OCH₃, or Cl

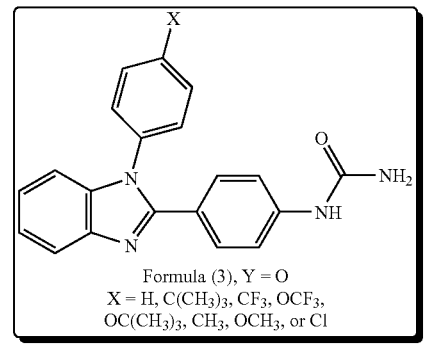

Formula (3), Y = O
X = H, C(CH₃)₃, CF₃, OCF₃, OC(CH₃)₃, CH₃, OCH₃, or Cl

Reagents: a) KF, K₂CO₃, MW; b) Zn, NH₄Cl, anhydrous CH₃OH, Δ or SnCl₂, HCl, CH₃OH; c) N(CH₂CH₃)₃, THF, room temp.; d) Ethyl acetate, Δ; e) SnCl₂, HCl, CH₃OH; f) CNNH₂, 1N HCl, Δ; g) Acetic Acid, H₂O, CH₃CH₂OH, NaOCN.

The compounds of formula 6 wherein Ar is 1-napthylenyl; 2-napthylenyl; phenanthrenyl; anthracenyl,

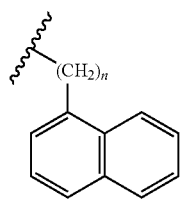

wherein n is 0, 1, 2, or 3; or other analogs disclosed herein can be generated in a similar fashion as illustrated in Scheme 2, with the selection of an appropriate analog of compound 110 in the reaction scheme.

Example 4

Synthesis of Cycloaliphatic-Substituted Benzimidazole Compounds of Formula 7

The preparation of the cycloaliphatic-substituted benzimidazole compounds may be accomplished using the synthetic route illustrated in Scheme 3. Under microwave irradiation, the alkyl substituted amine 119 may be coupled to 1-fluoro-2-nitrobenzene 109 to give the nitro diaryl amine 120. The nitro group of the diaryl amine may be reduced using zinc and ammonium chloride to produce the diamine 121. Reacting the diamine and the benzoyl chloride 113 together under reflux conditions could generate compounds of formula 7. For general information, see: Goker, H. et al., *Bioorganic. Medicinal Chemistry* 2002, 10, 2589-2596. The resulting molecules may be purified using a combination of flash chromatography and/or recrystallization.

Scheme 3

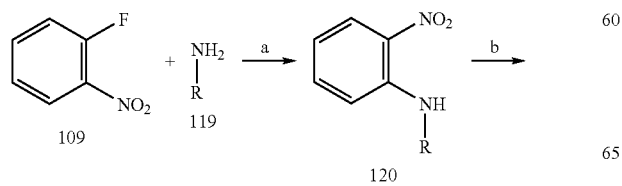

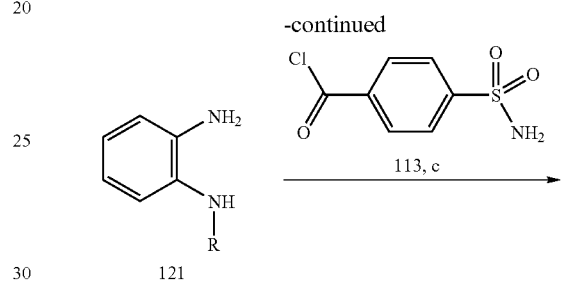

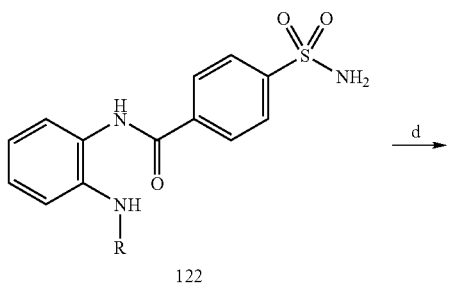

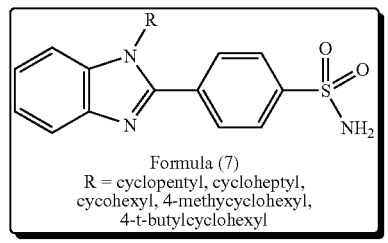

Formula (7)
R = cyclopentyl, cycloheptyl, cyclohexyl, 4-methycyclohexyl, 4-t-butylcyclohexyl Reagents: a) K₂CO₃, MW; b) Zn, NH₄Cl, anhydrous CH₃OH, Δ or SnCl₂, HCl, CH₃OH; c) N(CH₂CH₃)₃, THF, room temp.; d) Ethyl acetate, Δ.

Example 5

Synthesis of Cycloaliphatic-Substituted Benzimidazole Compounds of Formula 8

Compounds of formula

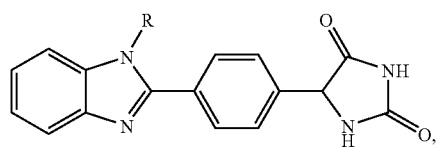
(8)

can be prepared according to Scheme 3, using the benzoyl chloride

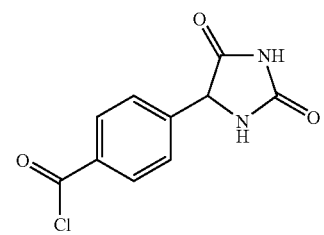

for preparing the compounds.

Example 6

Synthesis of Cycloaliphatic-Substituted Benzimidazole Compounds of Formula 9

The preparation of aromatic-substituted benzimidazole compounds of formula 9 was accomplished using the synthetic route outlined in Scheme 4. Under microwave irradiation, a 4-substituted aniline derivative 119 was coupled to 1-fluoro-2-nitrobenzene 109 to give a nitro diaryl amine 120 as previously described. The diaryl amine 120 can be reduced to the diamine 121. Subsequently, the diamine can be reacted with nitro substituted benzoic acid 115 to prepare the benzimidazole 124. The reduced product 125 can be converted to the desired guanidine and carbamide substituted benzimidazole. The resulting molecules were or could be purified using a combination of flash chromatography and/or recrystallization. The resulting compounds were or could be characterized by NMR spectroscopy, IR spectroscopy, melting point, and mass spectrometry.

Scheme 4

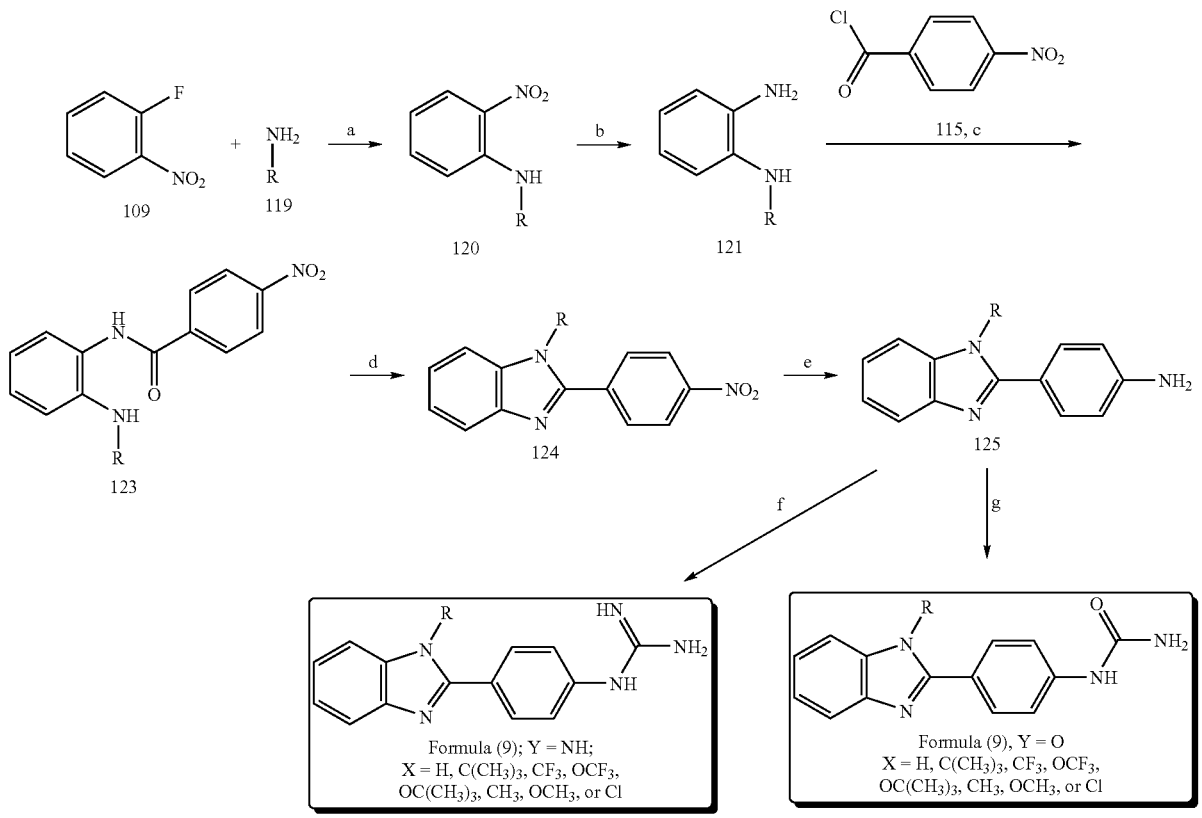

Reagents: a) KF, $K_2CO_3$, MW; b) Zn, $NH_4Cl$, anhydrous $CH_3OH$, Δ or $SnCl_2$, HCl, $CH_3OH$; c) $N(CH_2CH_3)_3$, THF, room temp.; d) Ethyl acetate, Δ; e) $SnCl_2$, HCl, $CH_3OH$; f) $CNNH_2$, 1N HCl, Δ; g) Acetic Acid, $H_2O$, $CH_3CH_2OH$, NaOCN.

Example 7

Synthesis of Sulfonamide-Substituted Imidazopyridine Compounds of Formula 10

The preparation of sulfonamide-substituted imidazopyridine analogs was accomplished using the synthetic route outlined in Scheme 5. Under microwave irradiation, a 4-substituted aniline derivative 110 was coupled to 1-fluoro-2-nitrobenzene 126 to give a nitro diaryl amine 127. Using a domestic microwave, the reaction produced yields greater than 99.5% when the aniline substituent was an electron donating group. (See: Xu, Z.; Lu, Y.; Guo, Z-R. *Synlett.*, 2003, 564-566.) However, optimizing the reaction conditions was difficult using a standard household microwave and relied heavily on the placement of the vessel in the microwave cavity to ensure reproducibility.

Scheme 5

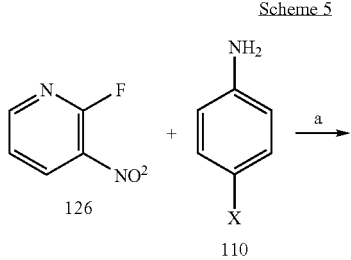

126    110

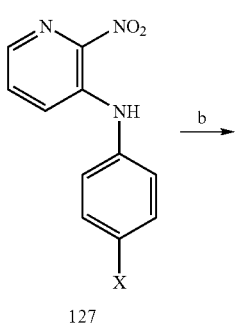

127

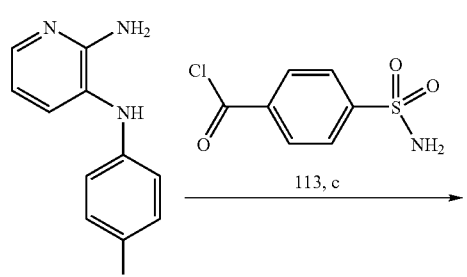

128

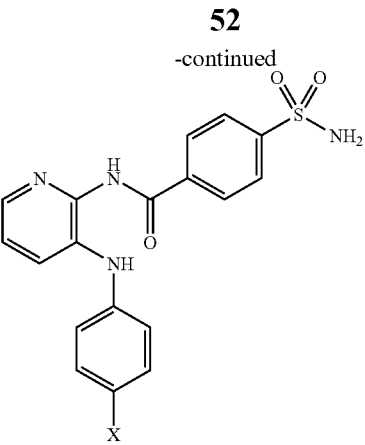

129

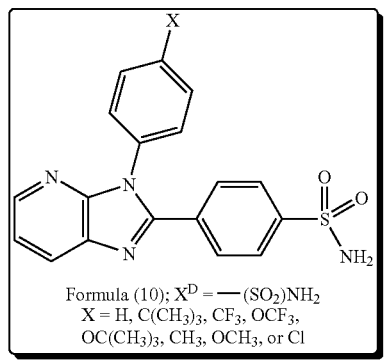

Formula (10); $X^D = -(SO_2)NH_2$
X = H, C(CH$_3$)$_3$, CF$_3$, OCF$_3$,
OC(CH$_3$)$_3$, CH$_3$, OCH$_3$, or Cl Reagents: a) KF, K$_2$CO$_3$, MW; b) Zn, NH$_4$Cl, anhydrous CH$_3$OH, Δ or SnCl$_2$, HCl, CH$_3$OH; c) N(CH$_2$CH$_3$)$_3$, THF, room temp.; d) Ethyl acetate, Δ.

When the reaction was conducted in the CEM Discovery System, a single mode industrial microwave able to maintain the temperature and pressure of the reaction mixture, the reaction time was decreased from 20 minutes to 5 minutes in some cases. The CEM reaction gave reproducible results and the crude reaction mixture showed no evidence of side products. The nitro group of the diaryl amine was reduced using zinc and ammonium chloride. After about 24 hours, approximately 90-100% of the nitro compound 127 was reduced to the diamine 128. Ring formation was afforded from a condensation reaction of the diamine and the benzoyl chloride 113 in two steps to give the target molecules 10. For general information, see: Goker, H.; Kus, C.; Boykin, D.; Yildiz, S.; Altanlar, N. Synthesis of Some New 2-Substituted-phenyl-1H-benzimidazole-5-carbonitriles and Their Potent Activity Against. *Candida* Species. *Bioorganic. Medicinal Chemistry* 2002, 10, 2589-2596. The analogs corresponding to formula 16, wherein $X^D$ is

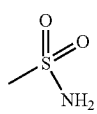

and wherein Ar is 1-napthylenyl; 2-napthylenyl; phenanthrenyl; anthracenyl;

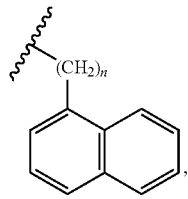

wherein n is 0, 1, 2, or 3; or other analogs disclosed herein can be generated in a similar fashion as illustrated in Scheme 1, with the selection of an appropriate analog of compound 110 in the reaction scheme. The resulting compounds were or could be characterized by NMR spectroscopy, IR spectroscopy, melting point, and mass spectrometry.

Example 8

Synthesis of Sulfonamide-Substituted Imidazopyridine Compounds of Formulas 11, 12, and 13

Scheme 5 can be applied towards the synthesis of compounds of formulas 11, 12, and 13 wherein $X^D$ is

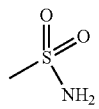

using the appropriate halogen substituted nitro pyridine

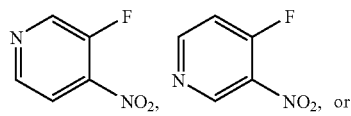

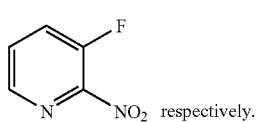

respectively.

Example 9

Synthesis of Hydantoin-Substituted Imidazopyridine Compounds of Formulas 10, 11, 12 and 13

The following compounds of formulas 10, 11, 12, and 13:

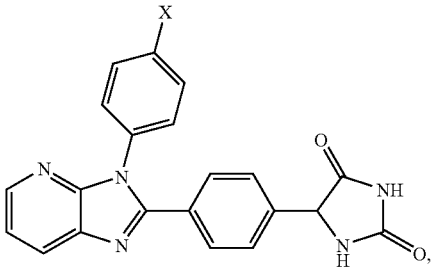

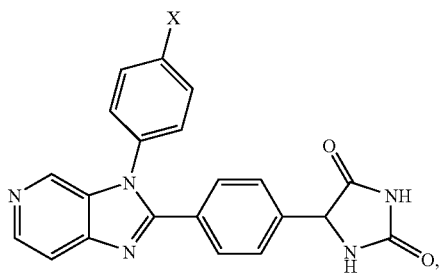

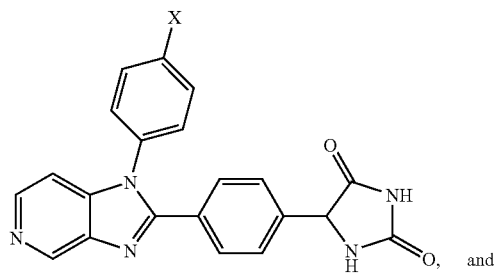

and

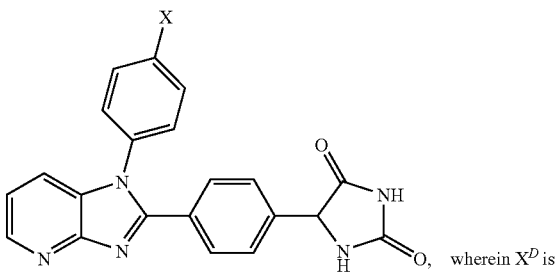

wherein $X^D$ is

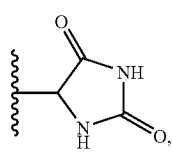

can be prepared according to Scheme 5, using the benzoyl chloride

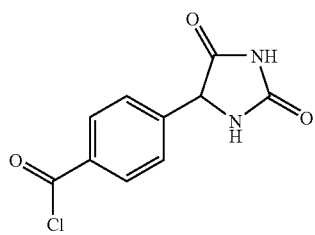

for preparing the compounds, and the appropriate halogen-substituted nitro pyridine as described above.

Example 10

Synthesis of Guanidine and Carbamide-Substituted Imidazopyridine Compounds of Formula 10

The preparation of aromatic-substituted benzimidazole analogs was accomplished using the synthetic route outlined in Scheme 6. Under microwave irradiation, a 4-substituted aniline derivative 110 was coupled to 1-fluoro-2-nitrobenzene 126 to give a nitro diaryl amine 127 as previously described. The diaryl amine 127 can be reduced to the diamine 128. Subsequently, the diamine can be reacted with nitro substituted benzoic acid 115 to prepare the benzimidazole 117. The reduced molecule 118 can be converted to the desired guanidine and carbamide substituted benzimidazole. The resulting molecules 10 may be purified using a combination of flash chromatography and/or recrystallization.

Scheme 6

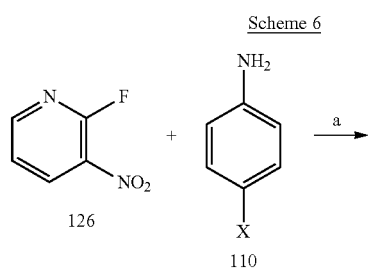

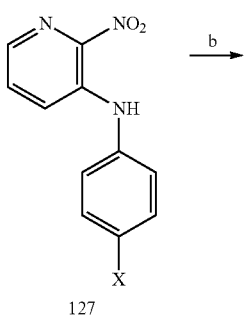

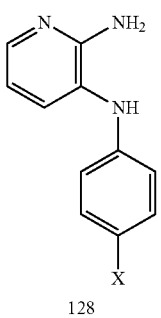

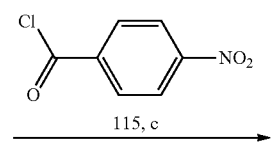

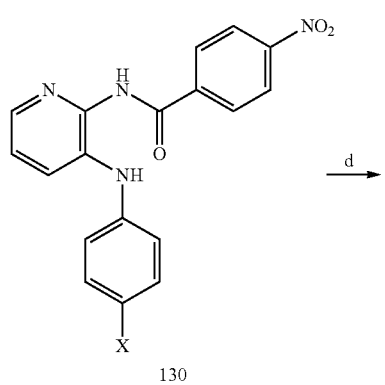

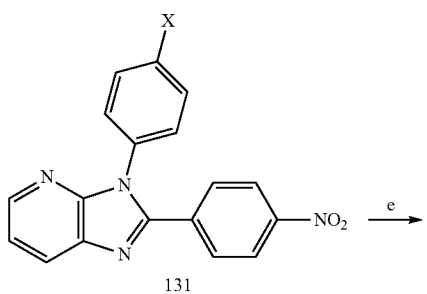

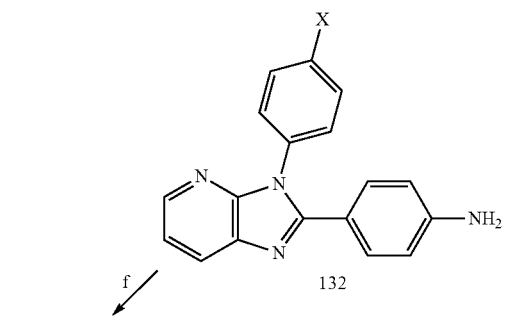

-continued

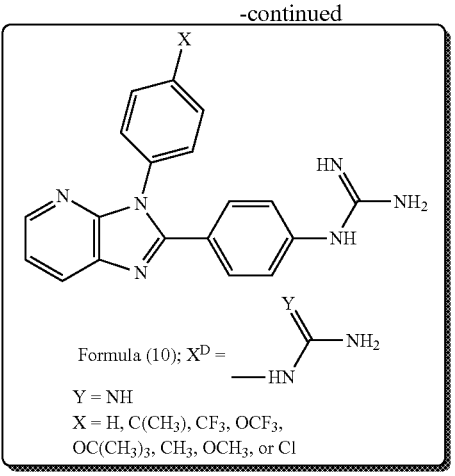

Formula (10); $X^D =$
Y = NH
X = H, C(CH$_3$), CF$_3$, OCF$_3$,
OC(CH$_3$)$_3$, CH$_3$, OCH$_3$, or Cl

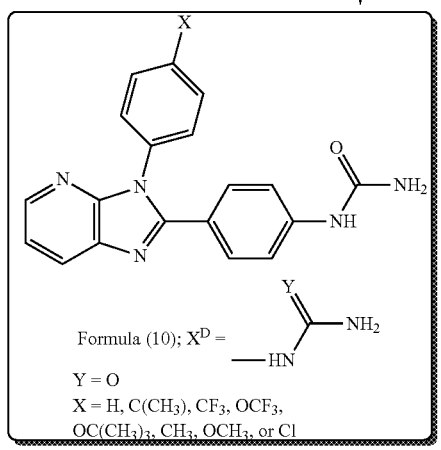

Formula (10); $X^D =$
Y = O
X = H, C(CH$_3$), CF$_3$, OCF$_3$,
OC(CH$_3$)$_3$, CH$_3$, OCH$_3$, or Cl Reagents: a) KF, K$_2$CO$_3$, MW; b) Zn, NH$_4$Cl, anhydrous CH$_3$OH, Δ or Sn Cl$_2$, HCl, CH$_3$OH; c) N(CH$_2$CH$_3$)$_3$, THF, room temp.; d) Ethyl acetate, Δ; e) SnCl$_2$, HCl, CH$_3$OH; f) CNNH$_2$, 1N HCl, Δ; g) Acetic Acid, H$_2$O, CH$_3$CH$_2$OH, NaOCN.

Derivatives compounds of formula 16, wherein $X^D$ is

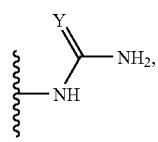

wherein Ar is 1-napthylenyl; 2-napthylenyl; phenanthrenyl; anthracenyl;

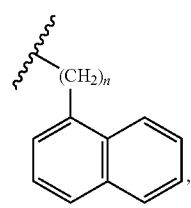

wherein n is 0, 1, 2, or 3, or other analogs disclosed herein can be generated in a similar fashion as illustrated in Scheme 1, with the selection of an appropriate analog of compound 110 in the reaction scheme.

Example 11

Synthesis of Sulfonamide-Substituted Imidazopyrazines and Sulfonamide-Substituted Purines of Formulas 14, 15, 20 and 21

Scheme 5 can be applied towards the synthesis of the following compounds of formulas 14 and 20:

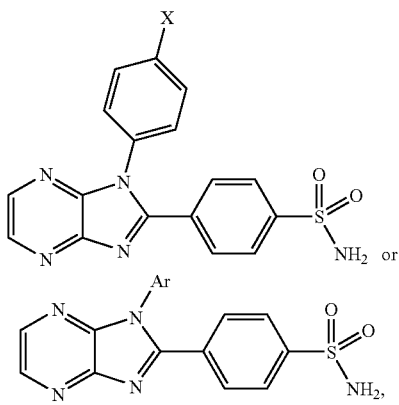

by using

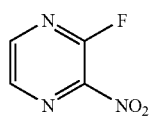

instead of 126. Scheme 5 can also be applied towards the synthesis of the following compounds of formulas 15 and 21:

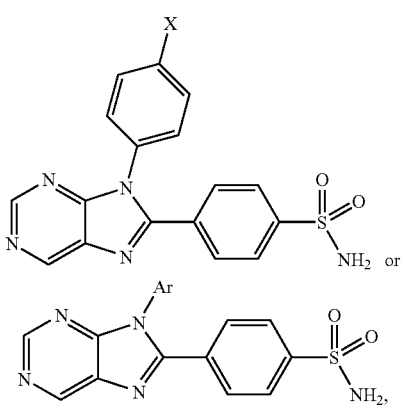

by using

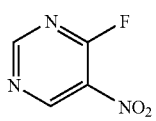

instead of 126.

Example 12

Synthesis of Hydantoin-Substituted Imidazopyrazines and Hydantoin-Substituted Purines of Formulas 14, 15, 20 and 21

The following compounds of formulas 14, 15, 20, and 21:

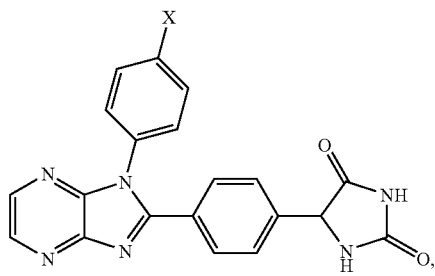

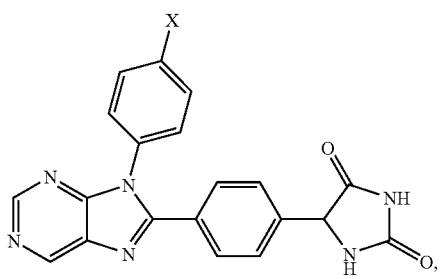

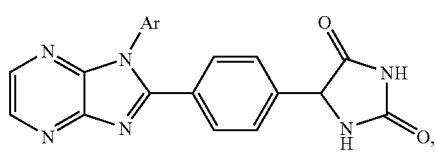

and

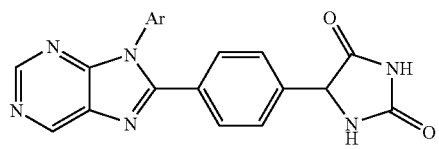

can be prepared according to Scheme 5, using the benzoyl chloride

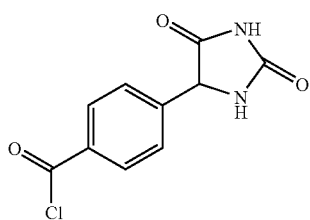

for preparing the compounds.

Example 13

Synthesis of Guanidine/Carbamide-Substituted Imidazopyrazines and Guanidine/Carbamide-Substituted Purines of Formulas 14, 15, 20 and 21

Scheme 6 can be applied towards the synthesis of the following compounds of formulas 14 and 20:

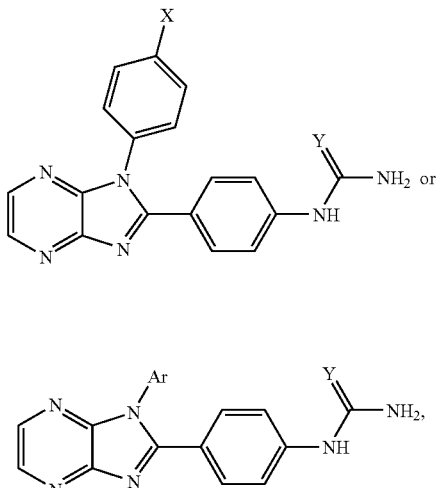

with the use of

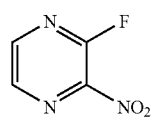

instead of 126. Scheme 6 can also be applied towards the synthesis of the following compounds of formulas 15 and 21:

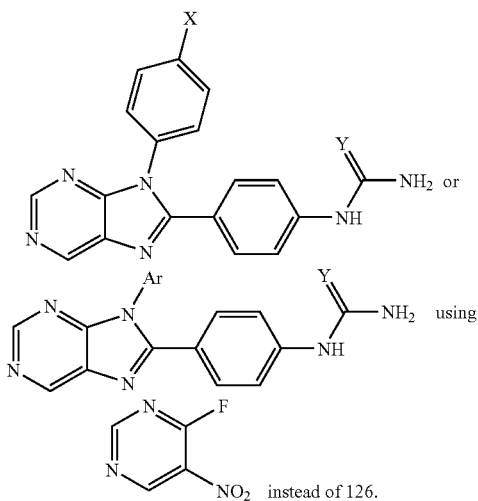

instead of 126.

Example 14

Synthesis of 7-Aromatic-Substituted Benzimidazole Compounds of Formula 22

The preparation of 7-aromatic-substituted benzimidazole compounds having the formula 22 may be accomplished using the synthetic route outlined in Scheme 7. Thus, compounds having the formula

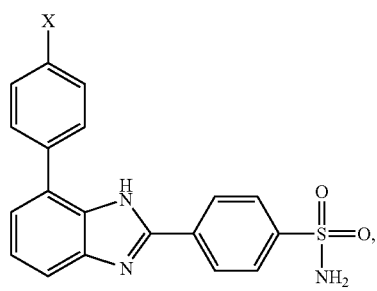

(22)

in which X can be selected from H, C(CH$_3$)$_3$, phenyl, CF$_3$, OCF$_3$, OC(CH$_3$)$_3$, CH$_3$, OCH$_3$, or Cl, and other aryl groups disclosed herein can be synthesized as follows.

Compounds of formula 22 can be prepared by an initial carbon-carbon coupling of two aromatic rings, Scheme 7, according to the method disclosed in Ito, Y.; Kojima, Y.; Suginome, M.; Murakami, M. New Synthesis of Quinoxaline Derivatives Based on Palladium Catalyzed Oligomerization of 1,2-diisocyanoarenes. *Heterocycles* 1996, 42, 597-615. The heteroaromatic ring can then be reduced using lithium aluminum hydride. Completion of the synthesis can occur with a microwave catalyzed condensation to form the benzimidazole ring, to provide the compounds of formula 22.

Scheme 7

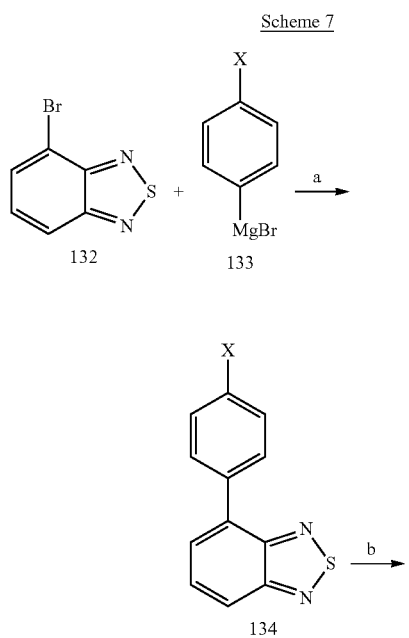

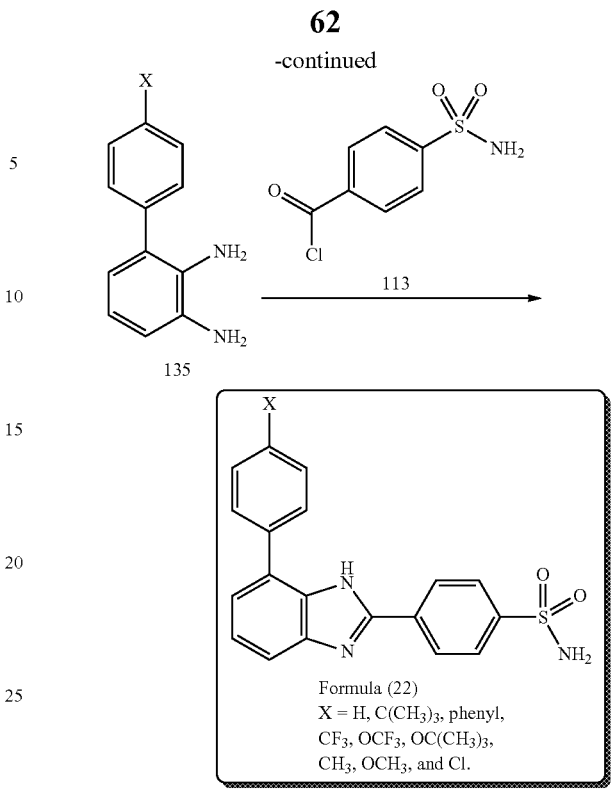

Reagents: a) ZnCl$_2$, [1,1'-Bis(diphenylphosphino)ferrocene] dichloropalladium (II), THF; b) LiAlH$_4$, THF The Grignard reagent of Scheme 7 and the thiadiazole protected diaryl amine are readily available, and the reaction is known to proceed in yields greater than about 55%. Therefore, the Grignard approach is one desired route for preparing compounds of formula 22, and there should be few side reaction products involving the thiadiazole ring.

Example 15

Alternative Syntheses of 7-Aromatic-Substituted Benzimidazole Compounds of Formula 22

In an alternative reaction sequence, aromatic-substituted benzimidazole compounds of formula 22 may be prepared through the synthesis of compound 134 according to Scheme 7. Compound 134 prepared in this manner then may be used in the synthetic route according to Scheme 8. According to this method, compound 134 may be prepared from 132 utilizing a Suzuki cross-coupling aided by an aryl boronic acid 135 and a palladium phosphine catalyst (such as Pd(PPh$_3$)$_4$, as illustrated Scheme 8).

Scheme 8

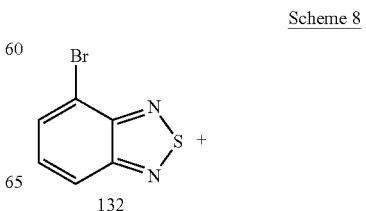

63

-continued

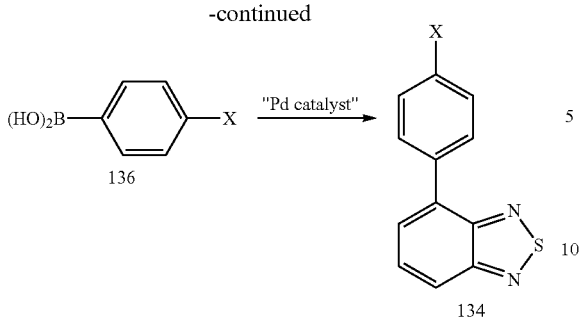

Example 16

Synthesis of 7-Aromatic-Substituted Benzimidazole Compounds of Formula 23

Compounds of the formula

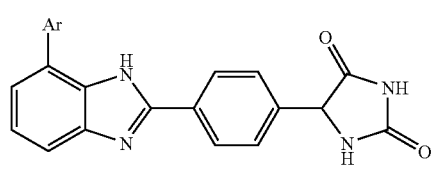
(23)

can be prepared according to Scheme 7, using the benzoyl chloride

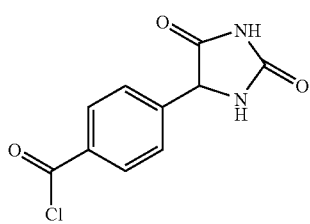

for preparing the compounds.

64

Example 17

Synthesis of 7-Aromatic-Substituted Benzimidazole Compounds of Formula 27

The preparation of 7-aromatic-substituted benzimidazole compounds having the formula

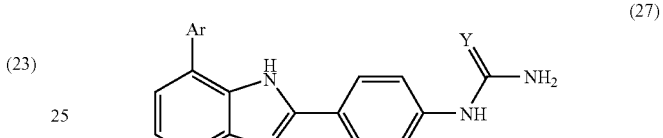
(27)

may be accomplished from compound 135 using the synthetic route outlined in Scheme 9. Compound 135 can be prepared by methods previously described. According to the method, compound 135 can be condensed with the nitro benzoic acid 115 to form the benzimidazole 137. The reduced molecule 138 can be converted to the desired guanidine and carbamide substituted benzimidazole. The resulting molecules may be purified using a combination of flash chromatography and/or recrystallization.

Scheme 9

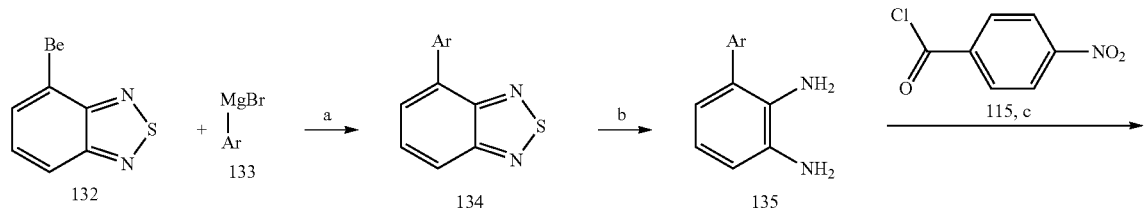

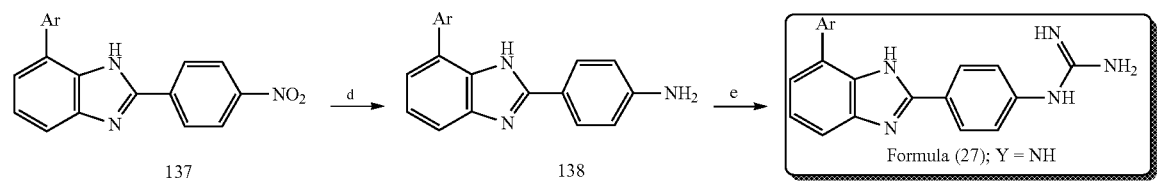

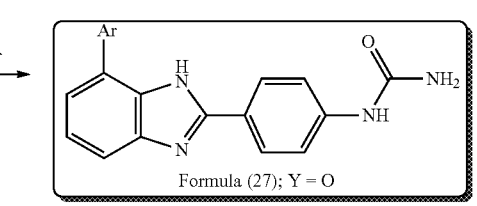

Formula (27); Y = O

Reagents: a) ZnCl₂, [1,1′-Bis(diphenylphosphino)ferrocene]dichloropalladium (II), THF; b) LiAlH₄, THF; c) microwave; d) SnCl₂, HCl, CH₃OH; e) CNNH₂, 1N HCl, Δ; f) Acetic Acid, H₂O, CH₃CH₂OH, NaOCN.

Example 18

Alternative Syntheses of Aromatic-Substituted Benzimidazole Compounds of Formulas 3 and 6

Alternative syntheses of preparing the aromatic-substituted benzimidazole compounds of formulas 3 and 6 can be carried out as follows. Referring to Scheme 10, which specifically illustrates the alternative synthesis for compounds of formula 3, benzoyl chloride (140) may used to accomplish the cyclization to form the benzimidazole. However, the yields are less than those obtained for the method described in Scheme 2.

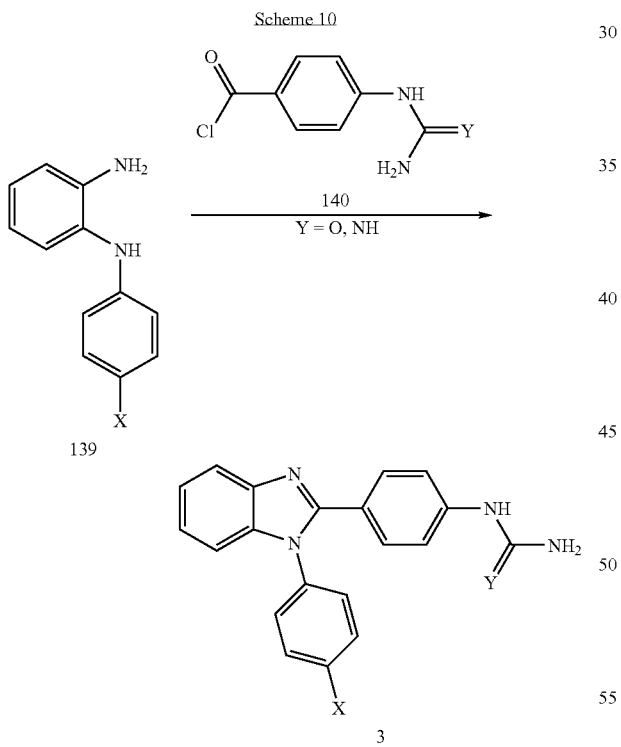

Alternatively, a benzoic acid may be used in place of the benzoyl chloride for the cyclization reaction shown in Scheme 11. The reactions illustrated in Scheme 11 are also applicable to compounds of formulas 1-2 and 4-5, while utilizing the appropriate substitutions. The alternative is also useful in the preparation of compounds of formulas 10-20 when the appropriate diamine precursor is used. Another alternative reaction carries out the cyclization in the presence of a sodium bisulfite adduct of the appropriately substituted benzaldehyde (141e). These reactions may be conducted using the one-step microwave procedure disclosed herein, or alternatively, under reflux conditions to produce the desired final product. Additional alternative cyclization reagents for reaction with the diaryl amine include the imidate (141b), amide (141c) or nitrile (141d), in which $R^F$, $R^G$, and $R^H$ are selected independently from H, an alkyl having up to about 10 carbon atoms, or an aryl group having up to about 14 carbons.

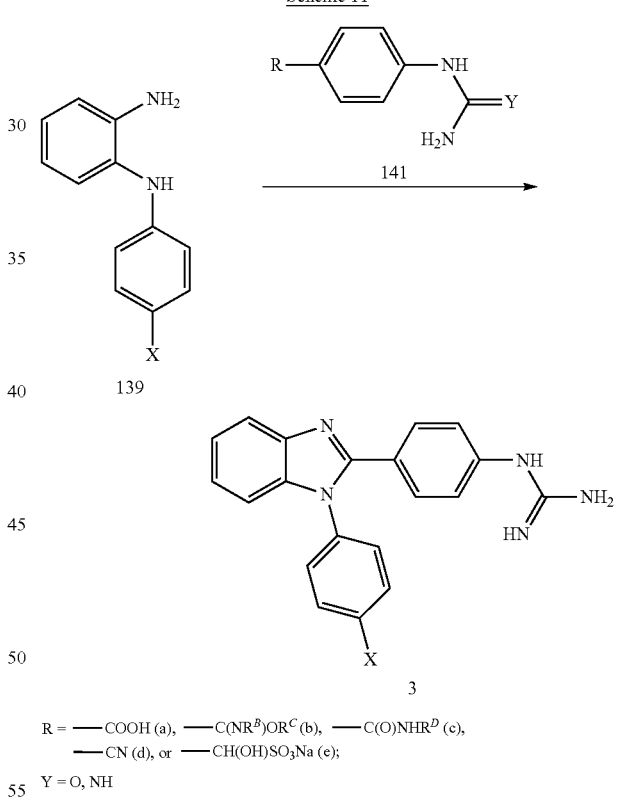

Example 19

Spectral and Analytical of Molecules $^1$H NMR spectral data for the molecules was on a Varian INOVA 400 MHz spectrometer. Chemical shifts are expressed relative to tetramethylsilane (TMS) and deuterated acetone.

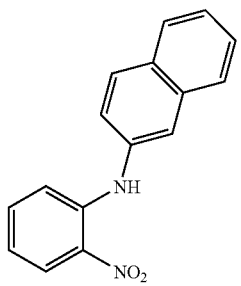

N-(2-nitrophenyl)-2-naphthalenamine was obtained in 43% yield as a yellow solid. m/z 265.1 (M+H)+. $^1$H NMR (CDCl$_3$, 400 MHz) δ 6.79 (t, J=15.2 Hz, 1H); 7.31 (d, J=8.8 Hz, 1H); 7.37-7.41 (m, 2H); 7.47-7.51 (m, 2H); 7.72 (sd, J=1.6 Hz, 1H); 7.78 (d, J=7.2 Hz, 1H); 7.84 (d, J=7.6 Hz, 1H); 7.88 (d, J=8.4 Hz, 1H); 8.22 (dd, J=10, 1.6 Hz, 1H); 9.5 (br s, 1H).

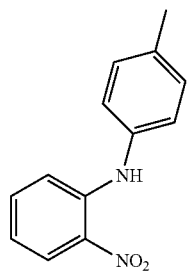

4-Methyl-2'-nitrodiphenylamine was obtained as an orange solid. IR (mineral oil) 1507.34, 1598.48, 2343.80, 2918.48, 3030.66, 3316.19 cm$^{-1}$. $^1$H NMR (CDCl$_3$, 400 MHz) δ 2.4 (s, 3H); 6.71 (t, J=6.8 Hz, 1H); 7.13-7.26 (m, 5H); 7.32 (t, J=6.8 Hz, 1H); 8.18 (dd, J=8.4, 1.6 Hz, 1H); 9.46 (br s, 1H).

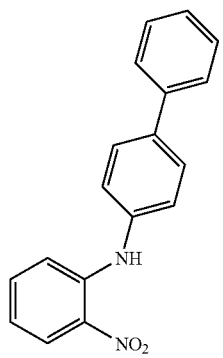

4-Phenyl-2'-nitrodiphenylamine was obtained as an orange solid. $^1$H NMR (CDCl$_3$, 400 MHz) δ 6.78 (t, J=6.8 Hz, 1H); 7.31-7.43 (m, 6H); 7.45 (t, J=6.4 Hz, 2H); 7.60-7.66 (m, 5H); 8.22 (dd, J=8.8, 1.2 Hz, 1H); 9.54 (s, 1H).

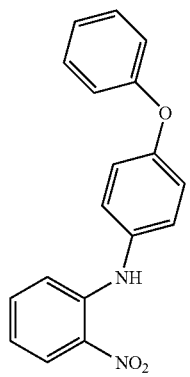

4-Phenoxy-2'-nitrodiphenylamine was obtained as an red solid. $^1$H NMR (CDCl$_3$, 400 MHz) δ 6.74 (t, J=7.2 Hz, 1H); 7.04-7.16 (m=5); 7.23 (m, 3H); 7.35 (m, 3H); 8.19 (dd, J=8.8, 1.2 Hz); 9.45 (br s, 1H).

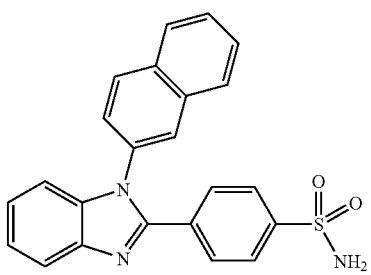

(208)

4-[1-(2-Napthalenyl)-1H-benzimidazol-2-yl)]Benzene-sulfonamide (208) was obtained as a white solid. m/z 400.1 (M+H)+. $^1$H NMR (CD$_3$COCD$_3$, 400 MHz) δ 6.85 (d, J=8 Hz, 1H); 7.17-7.23 (m, 2H); 7.32 (t, J=14.4 Hz, 1H); 7.43 (t, J=16 Hz, 1H); 7.56 (t, J=15.2 Hz, 1H); 7.68-7.73 (m, 6H); 7.84 (d, J=7.2 Hz, 1H); 8.11 (d, J=8.4 Hz, 1H); 8.17 (q, J=9.6 Hz, 1H).

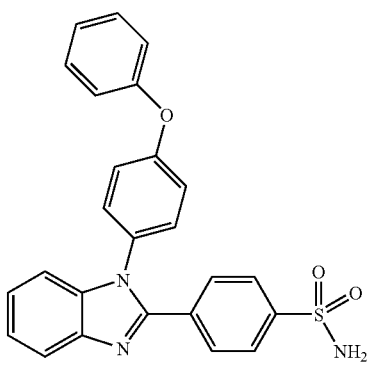

(210)

4-(1-Phenoxy-1H-benzimidazol-2-yl)Benzenesulfona-mide (210) was obtained as a white solid. $^1$H NMR (DMSO, 400 MHz) δ 7.2 (d, J=6.8 Hz, 1H); 7.29-7.45 (m, 11H); 7.69 (d, J=8.8 Hz, 2H); 7.78 (d, J=8.8 Hz, 2H); 7.82 (m, 1H).

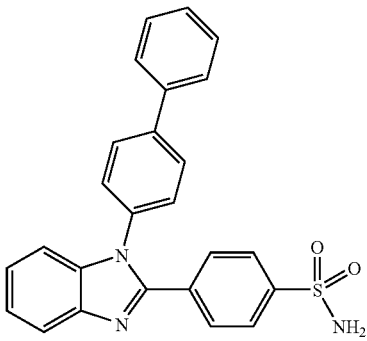

4-(1-Phenyl-1H-benzimidazol-2-yl)benzenesulfonamide (211) was obtained as a white solid. $^1$H NMR (DMSO, 400 MHz) δ

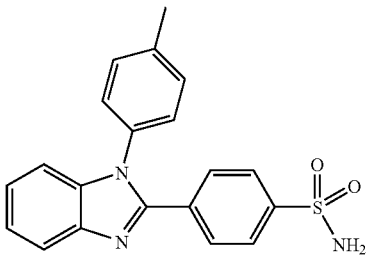

4-[1-(4-methylphenyl)-1H-benzo[d]imidazol-2-yl]benzenesulfonamide (206) was obtained as a white solid. $^1$H NMR (DMSO, 400 MHz) δ 2.3 (s, 3H); 7.2 (d, J=6.8 Hz, 1H); 7.29-7.45 (m, 6H); 7.69 (d, J=6.4, 2H); 7.79-7.85 (m, 3H).

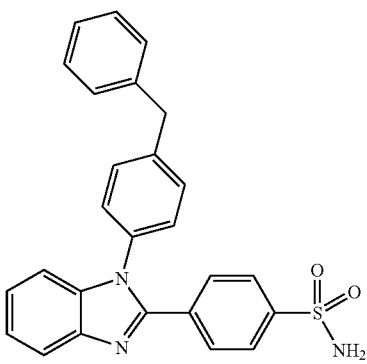

4-(1-(4-benzylphenyl)-1H-benzo[d]imidazol-2-yl)benzenesulfonamide (209) was obtained as an off-white solid. $^1$H NMR (DMSO, 400 MHz) δ 4.23 (s, 2H); 7.20-7.47 (m, 1H); 7.7 (d, J=8.4 Hz, 2H); 7.79 (d, J=8.4 Hz, 2H); 7.82 (d, J=8.0 Hz); 8.01-8.05 (m, 1H).

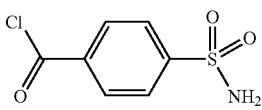

4-Sulfamoylbenzoyl chloride was obtained as a white solid. IR (mineral oil) 1157.02, 1340.30, 1719.63, 2964.05, 3252.65, 3331.67 cm$^{-1}$. $^1$H NMR (DMSO, 400 MHz) δ 7.54 (s, 1H); 7.92 (d, J=8.0 Hz, 2H); 8.10 (d, J=8.40 Hz, 2H).

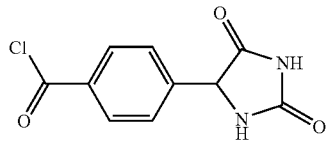

4-(2,5-dioxoimidazolidin-4-yl)benzoyl chloride was obtained as a tan solid. IR (mineral oil) $^1$H NMR (DMSO, 400 MHz) δ 3.28 (s, 1H); 5.291 (s, 1H); 7.45 (d, J=8.8 Hz, 2H); 7.96 (d, J=8.0 Hz 2H) 8.48 (s, 1H).

Example 20

Methods for Structural Analysis

Fuzzy Pharmacophore. A fuzzy pharmacophore was generated of OSU/Celecoxib analogs using the Pymol and the Liquid software plug-ins. See: DeLano, W. L. The PyMOL Molecular Graphics System (2002) DeLano Scientific, San Carlos, Calif., USA (www.pymol.org); Tanrikulu, Y.; Proschak, E.; Schneider G. LIQUID: Fuzzy Pharmacophore Models Based on Trivariate Gaussian Distributions, 2006, in preparation. The analysis of the inventive molecules was carried out by structural alignment, which was accomplished using the flexible alignment tool of MOE with default settings and the MMFF94. The molecules were docked in the crystal structure of PDK-1 in complex with ATP (PDB code 1H1W) using the GOLD software. See: a) Nissink, J.; Murray, C.; Hartshorn, M.; Verdonk, M.; Cole, J.; Taylor, R. A new test set for validating predictions of protein-ligand interaction. *Proteins* 2002, 49, 457-471; and b) GOLD-Protein-Ligand Docking www.ccdc.cam.ac.uk/products/life_sciences/gold/. The fuzzy pharmacophore was then generated for the docked structures with the highest GOLD score.

Overlays. The inventive molecules were further analyzed using overlays. Thus, the B3LYP hybrid functional with a double-zeta valence-polarization DFT basis set was used to perform DFT geometry optimizations on a 32-processor Xeon cluster using the NWChem computational chemistry program for parallel computers. See: *NWChem, A Computational Chemistry Package for Parallel Computers, Version* 5.0 (2006), Pacific Northwest National Laboratory, Richland, Wash. 99352-0999, USA; www.emsl.pnl.gov/docs/nwchem/nwchem.html. The benzimidazole and OSU structures were superimposed using the 'superpose' function in Tinker and seen to substantially coincide. Jay Ponder. Tinker Molecular Modeling Package, version 4.2. dasher.wustl.edu/tinker/.

Docking. The docking was accomplished using the crystal structure of PDK-1 complexed with ATP (PDB code 1H1W) subjected to the deletion of heteroatoms (phosphoserine, glycerol and sulfate ions), and the addition of polar hydrogens. Missing atoms were added to Gln73, Arg75, Arg238, Glu303, Lys304, Glu348, Lys357, and the missing residues Glu233, Ser234, Lys235 and Gln236 were added using DS Visualizer v1.6 and the Extensible Computational Chemistry Environment. See: *Accelrys®. www.accelrys.com/?lid=tab_accelrys* and *Extensible Computational Chemistry Environment. ecce.pnl.gov/*; Accelrys, Inc., 10188 Telesis Court, Suite 100, San Diego, Calif. 92121. The Gasteiger partial atomic charges and the gas-phase minimum energy structure were computed with MOE using the MM94x force field and default parameters. See: *Chemical Computing*

Group, Molecular Operating Environment (MOE); www.chemcomp.com/. MOE was used to designate the rotable bonds in the ligand and predict its bound conformations in the binding cavity. The docked protein-ligand structures with the most favorable hydrogen bonding to Ser160/Ala162, Glu209, Asp223 were then placed in a cubic solvent box and energy minimized in the same manner as the ATP-bound structure.

Calculation of Binding Energies. Binding affinities were calculated using the MM94x force field implemented in MOE by taking the difference between the energy of the bound system and the isolated protein and ligand using the optimized protein-ligand complexes described above. In all cases, the binding energies indicate favorable ligand binding.

Calculation of Lipophilicity and Molar Volume. The lipophilicities and molar volumes reported in Table 1 were calculated for the energy minimized structure contained in the database using the QuaSAR module in the MOE software.

Example 21

Methods for Biological Assay

Compounds 206-208 of Table 1 were analyzed for their ability to inhibit cell proliferation in human prostate cancer cells, the results of which are illustrated in FIG. 1. Compound 206 was slightly more effective at diminishing proliferation in PC-3 cells than its pyrazole counterpart celecoxib (201). Comparative test compounds 203-205 demonstrate an inhibition similar to that of the OSU compounds. See: Ripple M. O. et al., *Journal of the National Cancer Institute* 1997, 89, 40-48. Modest levels of kinase inhibition was observed for IKKβ and CK2. However, there was a significance reduction in activity for CDK1/cyclinB, GSK3β, and p70S6K in the presence of the benzimidazole compounds as illustrated in Table 2.

TABLE 2

Kinase Inhibition of Various Benzimidazole Compounds

| Kinase | % Activity (209) | % Activity (210) |
|---|---|---|
| CDK1/cyclinB(h) | 36 | 16 |
| CK2(h) | 22 | 99 |
| GSK3β(h) | 5 | 7 |
| IKKβ(h) | 25 | 72 |
| p70S6K(h) | 12 | 18 |
| PDK1(h) | 30 | Not tested |

| Kinase | % Activity (206) | % Activity (211) |
|---|---|---|
| CDK1/cyclinB(h) | 7 | 11 |
| CK2(h) | 92 | 99 |
| GSK3β(h) | 72 | 13 |
| IKKβ(h) | 86 | 71 |
| p70S6K(h) | 33 | 17 |
| PDK1(h) | Not tested | Not tested |

Cell Culture and Drug Treatment. PC-3 human prostate cancer cells were seeded in duplicate 96 well tissue culture plates at 500 cells/well in 80-μL Dulbecco's minimal essential medium (DMEM) supplemented with 5% fetal bovine serum (FBS) and nonessential amino acids and 1% equimolar mixture of streptomycin-penicillin. The flasks were incubated in a humidified 95% air/5% $CO_2$ atmosphere. The cells were grown for at least 24 hours to ensure that they were in the early log phase of growth. Cells were then treated with 20-μL drug solutions (stock 10 mM drug solution in DMSO was diluted in DMEM containing 5% FBS such that final DMSO concentration is less than 1%) of appropriate final concentration by serial dilution. Untreated control cells received 20-μL DMEM containing 5% FBS. Six wells of each plate received the same drug concentration. Thus, each data point and error bars are an average and standard deviation of readings from 12 wells treated with identical drug concentration.

DNA Assay. After appropriate time of incubation, DNA assay was performed. For DNA assay, each culture plate was washed with 25% PBS and incubated in deionized double distilled water for at least one hour at room temperature. Plates were frozen at −70° C. and thawed/equilibrated to room temperature. Hoechst 33258 DNA binding dye was then added to each well in 200-μL of high salt TNE buffer (10 mM Tris, 1 mM EDTA, 2 M NaCl [pH 7.4]) at a final concentration of 6.7-μg/mL. After further incubation at room temperature for 2 hours under protection from light, culture plates were scanned on the CytoFluor 2350™ scanner using the 360/460 nm filter excitation and emission set. Readings from all plates were normalized to the fluorescence of control untreated cells and all data were expressed as the percent control.

Kinase Assays. Kinase assays were conducted by Millipore's KinaseProfiler Service to determine the amount of ATP phosphorylation that occurs in the presence of a benzimidazole molecule. Kinases assayed included IKKβ, CK2, CDK1/cyclinB, GSK3β, and p70S6K. The desired kinase was treated with the benzimidazole compound The reaction were initiated by the addition of the MgATP mix. After incubation for 40 minutes at room temperature, the reaction is stopped by the addition of 3% phosphoric acid solution. 10 μL of the reaction was then spotted onto a P30 filtermat and washed three times for 5 minutes in 75 mM phosphoric acid and once in methanol prior to drying and scintillation counting. The kinase activity was measured radiometrically to determine the amount of ATP phosphorylation produced. All assays were done in triplicate.

The invention claimed is:
1. A compound having the formula:

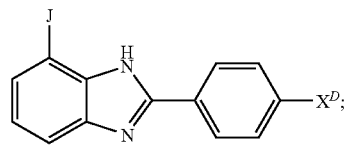

wherein J is selected from

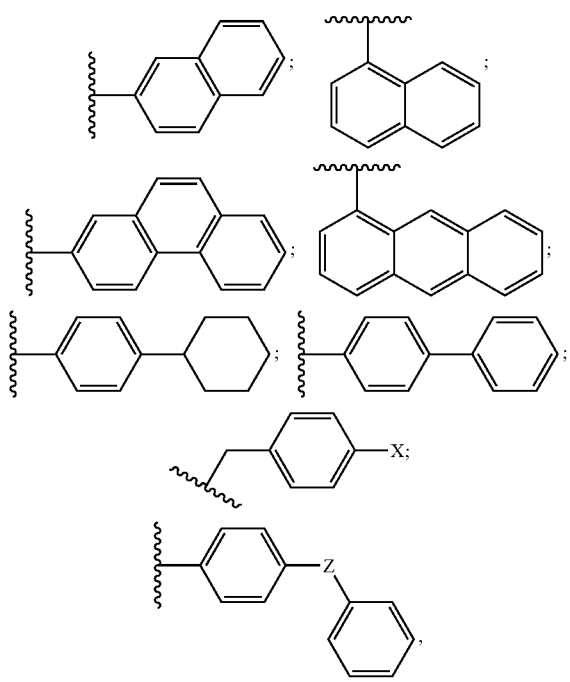

wherein Z is selected from $CH_2$, NH, O, or S;

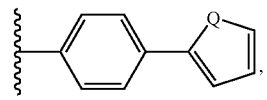

wherein Q is selected from $CH_2$, NH, O, or S;

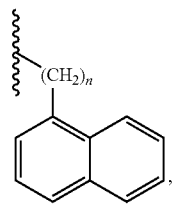

wherein n is 1, 2, or 3; or

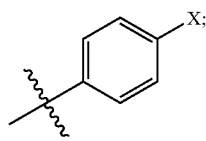

wherein X in each occurrence is selected from hydrogen; a halide; a linear or branched alkyl having up to 10 carbon atoms, optionally substituted with at least one halide; or an alkoxide having a linear or branched alkyl group having up to 10 carbon atoms, optionally substituted with at least one halide;

wherein $X^D$ is selected from

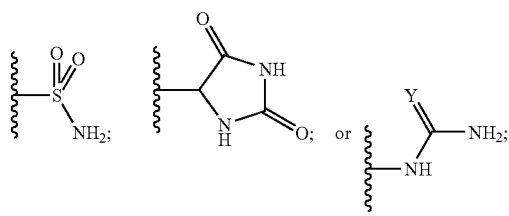

and Y is selected from O or NH.

2. A compound according to claim 1, having the formula:

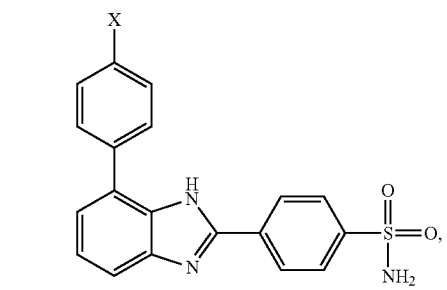

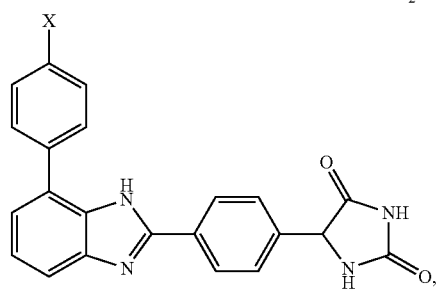

or

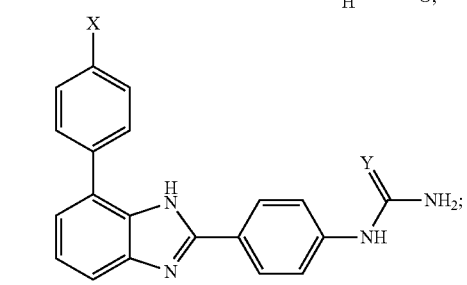

wherein X is selected from hydrogen; a halide; a linear or branched alkyl having up to 10 carbon atoms, optionally substituted with at least one halide; or an alkoxide having a linear or branched alkyl group having up to 10 carbon atoms, optionally substituted with at least one halide; and Y is selected from O or NH.

3. A compound according to claim 1 having the formula:

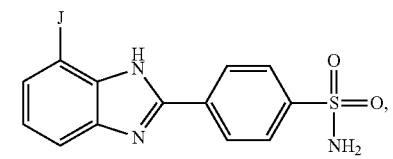

-continued

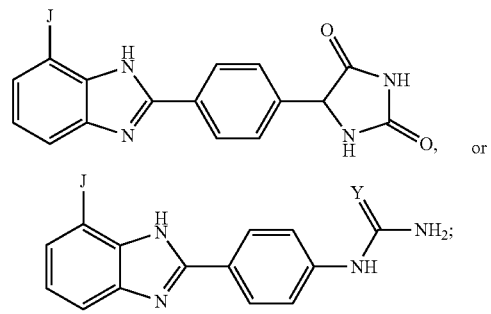

wherein J is selected from

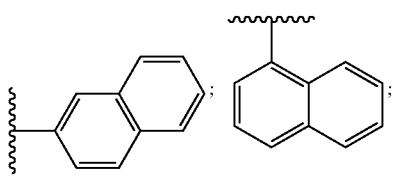

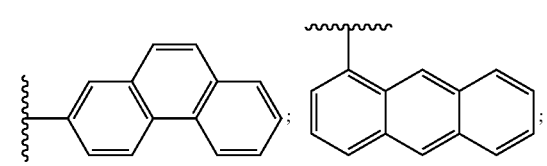

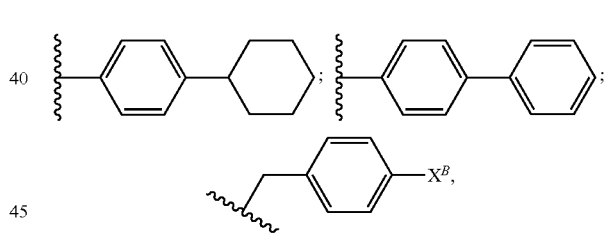

wherein X is selected from $CH_3$, $C(CH_3)_3$, or $OCH_3$;

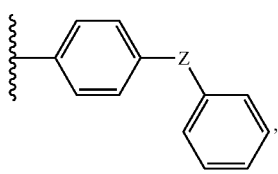

wherein Z is selected from $CH_2$, NH, O, or S;

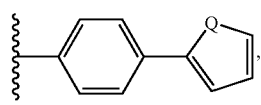

wherein Q is selected from CH$_2$, NH, O, or S; or
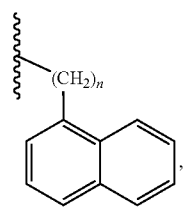
wherein n is 1, 2, or 3; and Y is selected from O or NH.
4. A pharmaceutical composition comprising a therapeutically-effective amount of at least one compound according to claim 1 or a pharmaceutically-acceptable salt thereof, and a pharmaceutically-acceptable carrier.
* * * * *

UNITED STATES PATENT AND TRADEMARK OFFICE
CERTIFICATE OF CORRECTION

| | | |
|---|---|---|
| PATENT NO. | : 7,947,723 B2 | Page 1 of 1 |
| APPLICATION NO. | : 12/363168 | |
| DATED | : May 24, 2011 | |
| INVENTOR(S) | : Leyte L. Winfield | |

It is certified that error appears in the above-identified patent and that said Letters Patent is hereby corrected as shown below:

At column 1, lines 9-17, replace the heading on "Government License Rights" and paragraph that follows with the following heading and paragraph:

--STATEMENT OF GOVERNMENT INTEREST

This invention was made with government support under Grant Award No. 5P20MD000215-07, awarded by the National Institutes of Health, National Institute on Minority Health and Health Disparities. The Government has certain rights in the invention.--

Signed and Sealed this
Twenty-second Day of May, 2012

David J. Kappos
*Director of the United States Patent and Trademark Office*